US006420031B1

(12) United States Patent
Parthasarathy et al.

(10) Patent No.: US 6,420,031 B1
(45) Date of Patent: *Jul. 16, 2002

(54) HIGHLY TRANSPARENT NON-METALLIC CATHODES

(75) Inventors: Gautam Parthasarathy, Princeton; Paul Burrows, Princeton Junction; Stephen R. Forrest, Princeton, all of NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/054,707

(22) Filed: Apr. 3, 1998

Related U.S. Application Data

(63) Continuation-in-part of application No. 08/964,863, filed on Nov. 5, 1997.
(60) Provisional application No. 60/064,005, filed on Nov. 3, 1997.

(51) Int. Cl.⁷ ............................. B32B 7/00; H05B 33/26
(52) U.S. Cl. .................. 428/411.1; 428/690; 428/917; 313/504; 313/506; 427/58; 427/66
(58) Field of Search ..................... 428/411.1, 690, 428/917; 313/504, 506; 427/58, 66

(56) References Cited

U.S. PATENT DOCUMENTS

| | | | |
|---|---|---|---|
| 4,356,429 A | 10/1982 | Tang | 313/503 |
| 5,203,974 A | 4/1993 | Kokado et al. | |
| 5,294,870 A | 3/1994 | Tang et al. | 313/504 |
| 5,424,560 A | 6/1995 | Norman et al. | 257/40 |
| 5,457,565 A | 10/1995 | Namiki et al. | 359/273 |
| 5,554,220 A | 9/1996 | Forrest et al. | |
| 5,703,436 A | 12/1997 | Forrest et al. | 313/506 |
| 5,707,745 A | 1/1998 | Forrest et al. | 428/432 |
| 5,714,838 A | 2/1998 | Haight et al. | 313/506 |
| 5,881,089 A | 3/1999 | Berggren et al. | 372/96 |
| 5,902,677 A | 5/1999 | Shi et al. | 428/332 |
| 6,015,631 A | 1/2000 | Park | 428/690 |
| 6,069,442 A | 5/2000 | Hung et al. | 313/504 |

FOREIGN PATENT DOCUMENTS

| EP | 0 704 915 | 4/1996 |
|---|---|---|

OTHER PUBLICATIONS

S. Tanaka et al., A Full Color Thin Film EL Device with Two Stacked Substrates and Color Filters, Proceedings of the Society for Information Displays, vol. 28, pp. 357–363, 1987. No month.

Tannas, Jr., Flat–Panel Displays and CRT's, Van Nostrand Reinhold Company, pp. 237–288. No month.

C.W. Tang et al., Appl. Phys. Lett. 51, pp. 913–915, Sep. 21, 1987.

S.R. Forrest, P.E. Burrows and M.E. Thompson, Laser Focus World, p. 99–107, Feb. 1995.

V. Bulovic, G. Gu, P.E. Burrows, M.E. Thompson, and S.R. Forrest, Nature 380, 29 (1996).

V. Bulovic, P. Tian, P.E. Burrows, M.R. Gokhale, and S.R. Forrest, Appl. Phys. Lett. 70, pp. 2954–2956, Jun. 2, 1997.

Z. Shen, P.E. Burrows, V. Bulovic, S.R. Forrest, and M.E. Thompson, Science 276, pp. 2009–2011, Jun. 27, 1997.

N. Karl, A. Bauer, J. Holzäofel, J. Marktanner, M. Möbus, and F. Stölzle, "Efficient Organic Photovoltaic Cells: The Role of Excitonic Light Collection, Exciton Diffusion to Interfaces, Internal Fields for Charge Separation, and High Charge Carrier Mobilities", Molecular Crystals and Liquid Crystals, vol. 252, pp. 243–258, 1994. (No month).

Whitlock, J.B., Panayotatos, P., Sharma, G.D., Cox, M.D., Savers, R.R., and Bird, G.R.; "Investigations of Materials and Device Structures for Organic Semiconductor Solar Cells," Optical Eng., vol. 32, No. 8, 1921–1934 (Aug. 1993).

P.E. Burrows, S.R. Forrest, Appl. Phys. Lett. 64, pp. 2285–2287, Apr. 25, 1994.

B.H. Schechtman and W.E. Spicer, J. of Mol. Spec. 33, pp. 28–48 (1970. (No month).

P.E. Burrows, Z. Shen, V. Bulovic, D.M. McCarty, S.R. Forrest, J.A. Cronin, and M.E. Thompson, J. Appl. Phys. 79, pp. 7991–8006, May 15, 1996.

S.R. Forrest, L.Y. Leu, F.F. So, and W.Y. Yoon, J. Appl. Phys. 66, pp. 5908–5914, Dec. 15, 1989.

A. Rajagopal, C.I. Wu, and A. Kahn, J. Appl. Phys. 83, pp. 2649–2655, Mar. 1, 1998.

K. Seki, Mol. Cryst. Liq. Cryst. 171, pp. 255–270 (1989). (No month).

(List continued on next page.)

*Primary Examiner*—Marie Yamnitzky
(74) *Attorney, Agent, or Firm*—Kenyon & Kenyon

(57) ABSTRACT

A novel class of low reflectivity, high transparency, non-metallic cathodes useful for a wide range of electrically active, transparent organic devices are disclosed. As a representative embodiment, the highly transparent non-metallic cathode of an OLED employs a thin film of copper phthalocyanine (CuPc) capped with a film of low-power, radio-frequency sputtered indium-tin-oxide (ITO). The CuPc prevents damage to the underlying organic layers during the ITO sputtering process. A theory of the invention is presented which suggests that damage-induced states at the non-metallic cathode/organic film interface are responsible for the efficient electron injection properties of the cathode. Due to the low reflectivity of the non-metallic cathode, a non-antireflection-coated, non-metallic-cathode-containing TOLED is disclosed that is 85% transmissive in the visible, emitting nearly identical amounts of light in the forward and back-scattered directions. The performance of the non-metallic-cathode-containing TOLED is found to be comparable to that of TOLEDs employing a more reflective and absorptive cathode consisting of a semi-transparent thin film of Mg:Ag capped with ITO.

70 Claims, 18 Drawing Sheets

OTHER PUBLICATIONS

F.F. So and S.R. Forrest, J. Appl. Phys. 63, pp. 442–446, Jan. 15, 1988.

G. Gu, V. Bulovic, P.E. Burrows, S.R. Forrest, and M.E. Thompson, Appl. Phys. Lett. 68, pp. 2606–2608, May 6, 1996.

S.A. Van Slyke, C.H. Chen, and C.W. Tang, Appl. Phys. Lett. 69, pp. 2160–2162, Oct. 7, 1996.

Parthasarathy, P.E. Burrows, V.G. Kozlov, and S.R. Forrest, "A Highly Transparent Organic Light Emitting Device Employing a Metal–Free Cathode," Poster Session Abstract, Materials Research Fair, Nov. 6, 1997, Princeton Materials Institute, Princeton University.

Stephen R. Forrest, "Ultrathin Organic Films Grown by Organic Molecular Beam Deposition and Related Techniques," Chemical Reviews, 97, 1793–1896, Sep./Oct. 1997.

HIGHLY TRANSPARENT NON-METALLIC CATHODES

CROSS-REFERENCE TO RELATED APPLICATIONS

This application is a continuation-in-part of copending Application Ser. No. 08/964,863, filed Nov. 5, 1997, which claims the benefit, under 35 U.S.C. 119(e), of U.S. Provisional Application Ser. No. 60/064,005, filed Nov. 3, 1997.

GOVERNMENT RIGHTS

This invention was made with Government support under Contract No. F33615-94-1-1414 awarded by DARPA. The government has certain rights in this invention.

FIELD OF INVENTION

The present invention is directed to non-metallic cathodes that may be used in optoelectronic devices, particularly, highly transparent non-metallic cathodes.

BACKGROUND OF THE INVENTION

Optoelectronic devices include those which convert electrical energy into optical energy, or vice versa, as well as those that detect optical signals through electronic processes. Such devices include photodetectors, phototransistors, solar cells, light emitting diodes and lasers. Such devices typically include a pair of electrodes with at least one charge-carrying layer between the electrodes. Dependent on the function of the device, the charge-carrying layer or layers may be comprised of a material or materials that are electroluminescent when a voltage is applied across the device or the layer or layers may form a heterojunction capable of generating a photovoltaic effect when exposed to optical radiation.

In particular, organic light emitting devices (OLEDs) are comprised of several organic layers in which one of the layers is comprised of an organic material that can be made to electroluminesce by applying a voltage across the device, C. W. Tang et al., *Appl. Phys. Lett* 51, 913 (1987). Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, February 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor.

A transparent OLED (TOLED), V. Bulovic, G. Gu, P. E. Burrows, M. E. Thompson, and S. R. Forrest, *Nature* 380, 29 (1996), which represents a significant step toward realizing high resolution, independently addressable stacked R-G-B pixels, was reported in U.S. Pat. No. 5,703,436, Forrest et al I. This TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag—ITO electrode layer for electron-injection. A device was disclosed in which the ITO side of the Mg—Ag—ITO electrode layer was used as a hole-injecting contact for a second, different color-emitting OLED stacked on top of the TOLED. Each layer in the stacked OLED (SOLED) was independently addressable and emitted its own characteristic color. This colored emission could be transmitted through the adjacently stacked transparent, independently addressable, organic layer, the transparent contacts and the glass substrate, thus allowing the device to emit any color that could be produced by varying the relative output of the red and blue color-emitting layers. U.S. Pat. No. 5,707,745, Forrest et al II, disclosed an integrated SOLED for which both intensity and color could be independently varied and controlled with external power supplies in a color tunable display device. Forrest et al II, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of injected electrons and holes. Specifically, OLEDs are comprised of at least two thin organic layers separating the anode and cathode of the device. The material of one of these layers is specifically chosen based on the material's ability to assist in injecting and transporting holes, a "hole transporting layer" (HTL), and the material of the other layer is specifically selected according to its ability to assist in injecting and transporting electrons, an "electron transporting layer" (ETL). With such a construction, the device can be viewed as a diode with a forward bias when the potential applied to the anode is more positive than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When, for example, an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

The materials that function as the electron transporting layer or as the hole transporting layer of the OLED are frequently the same materials that are incorporated into the OLED to produce the electroluminescent emission. Such devices in which the electron transporting layer or the hole transporting layer functions as the emissive layer are referred to as having a single heterostructure. Alternatively, the electroluminescent material may be present in a separate emissive layer between the hole transporting layer and the electron transporting layer in what is referred to as a double heterostructure.

The material that is used as the cathode layer of an OLED has until now been comprised of a metal which has a low work function, for example, Mg:Ag. Such metallic cathode layers provide an electrically conductive path for current flow as well as a means of injecting electrons into the adjacent electron transporting layer. However, such metallic layers are also highly reflective and absorptive in the visible region of the spectrum.

This means that if a transparent OLED is desired, such as for stacked layers of a full-color SOLED or the single OLED of a monochromatic TOLED, a balance needs to be established between metallic layers that are thick enough to function as a cathode, but not so thick as to cause substantial light transmission or reflection losses. A conventional TOLED, therefore, uses 75–100 Å Mg:Ag capped with a thick layer of sputter-deposited ITO; the Mg:Ag layer serving both to inject electrons into $Alq_3$ and to protect it from the ITO sputtering. Thus, although a device with about 70% transmission may be obtained, there is still significant reflection from the compound cathode. In addition, in SOLED devices in which at least one of the color-producing layers is contained between the metallic cathodes of adjacent color-producing OLEDs, microcavity effects are present which can give rise to color tuning problems. Z. Shen, P. E. Burrows, V. Bulovic, S. R. Forrest, and M. E. Thompson, *Science* 276, 2009 (1997). Such microcavity effects may also lead to an undesired angular dependence of the emitted light. Furthermore, thin Mg:Ag layers are sensitive to atmospheric degradation and, therefore, require special designs and processing steps to be undertaken so as to preserve their effectiveness in functioning as the cathode of an OLED.

Though solar cells have been disclosed in which a highly transparent ITO layer may have functioned as a cathode under certain circumstances, such ITO cathodes were disclosed as having been prepared by depositing the charge-carrying organic layer onto the ITO layer, N. Karl, A. Bauer, J. Holzäofel, J. Marktanner, M. Möbus, and F. Stölzle, "*Efficient Organic Photovoltaic Cells. The Role of Excitonic Light Collection, Exciton Diffusion to Interfaces, Internal Fields for Charge Separation, and High Charge Carrier Mobilities*", Molecular Crystals and Liquid Crystals, Vol. 252, pp 243–258, 1994 (Karl et al) and Whitlock, J. B., Panayotatos, P., Sharma, G. D., Cox, M. D., Savers, R. R., and Bird, G. R.; "*Investigations of Materials and Device Structures for Organic Semiconductor Solar Cells,*" Optical Eng., Vol. 32, No. 8, 1921–1934 (August 1993), (Whitlock et al). ITO layers on which the organic layer had been deposited would not have been expected to form a low-resistance electrical contact with the adjacent organic layer and, thus, would not have been expected to function, as confirmed hereinafter for OLEDs, as an efficient cathode.

It would be desirable if optoelectronic devices could be made using cathodes that are as highly transparent as the highly transparent ITO anodes. It would be desirable, furthermore, that such highly transparent cathodes still have, for example, in OLEDs, electron-injection characteristics comparable to the thin, semi-transparent, low-work-function metallic layers, such as Mg:Ag, that are typically used as the cathode layer.

ADVANTAGES AND SUMMARY OF THE INVENTION

The present invention is directed to cathodes comprised of an electrically conductive non-metallic layer in low-resistance contact with a semiconductive organic layer.

The present invention is directed toward highly transparent non-metallic cathodes that may be used in substantially any type of optoelectronic device.

More specifically, the present invention is directed to highly transparent non-metallic cathodes that may be used, for example, in OLEDs that have electron-injection properties comparable to semi-transparent metallic cathodes but which, instead, have an optical transmission of up to at least about 85% or still higher.

Still more specifically, the present invention is directed to a highly transparent organic light emitting device (OLED) comprised of a non-metallic cathode.

In another embodiment, the present invention is directed to an OLED comprised of an inorganic semiconducting material, such as ITO, that functions as the non-metallic cathode.

In yet another embodiment, the present invention is directed to organic semiconducting lasers comprised of a non-metallic cathode.

In still another aspect of the present invention, the OLED is comprised of a non-metallic cathode which is in contact with an organic protection layer that is capable of assisting in the injection and transport of electrons from the cathode to the luminescent zone of the OLED and that is, furthermore, capable of protecting the underlying organic layers from damage during deposition of the cathode layer. This organic protection layer may be in direct contact with the electron transporting layer in the luminescent zone of the device or there may be an additional electron transporting layer between these two layers which further assists in transporting electrons to the luminescent zone of the OLED.

In still another aspect of the present invention, the present invention is directed to a method for fabricating a cathode comprising preparing a cathode comprised of an electrically conductive non-metallic layer and a semiconductive organic layer, wherein the preparation includes the step of forming a region between the electrically conductive non-metallic layer and the semiconductive organic layer that causes the electrically conductive non-metallic material to be in low-resistance electrical contact with the semiconductive organic layer.

In addition, the present invention is directed to a method of fabricating an organic light emitting device comprised of a non-metallic cathode.

Further objectives and advantages of the present invention will be apparent to those skilled in the art from the detailed description of the disclosed invention.

DETAILED DESCRIPTION OF THE PREFERRED EMBODIMENTS

Figure 1:
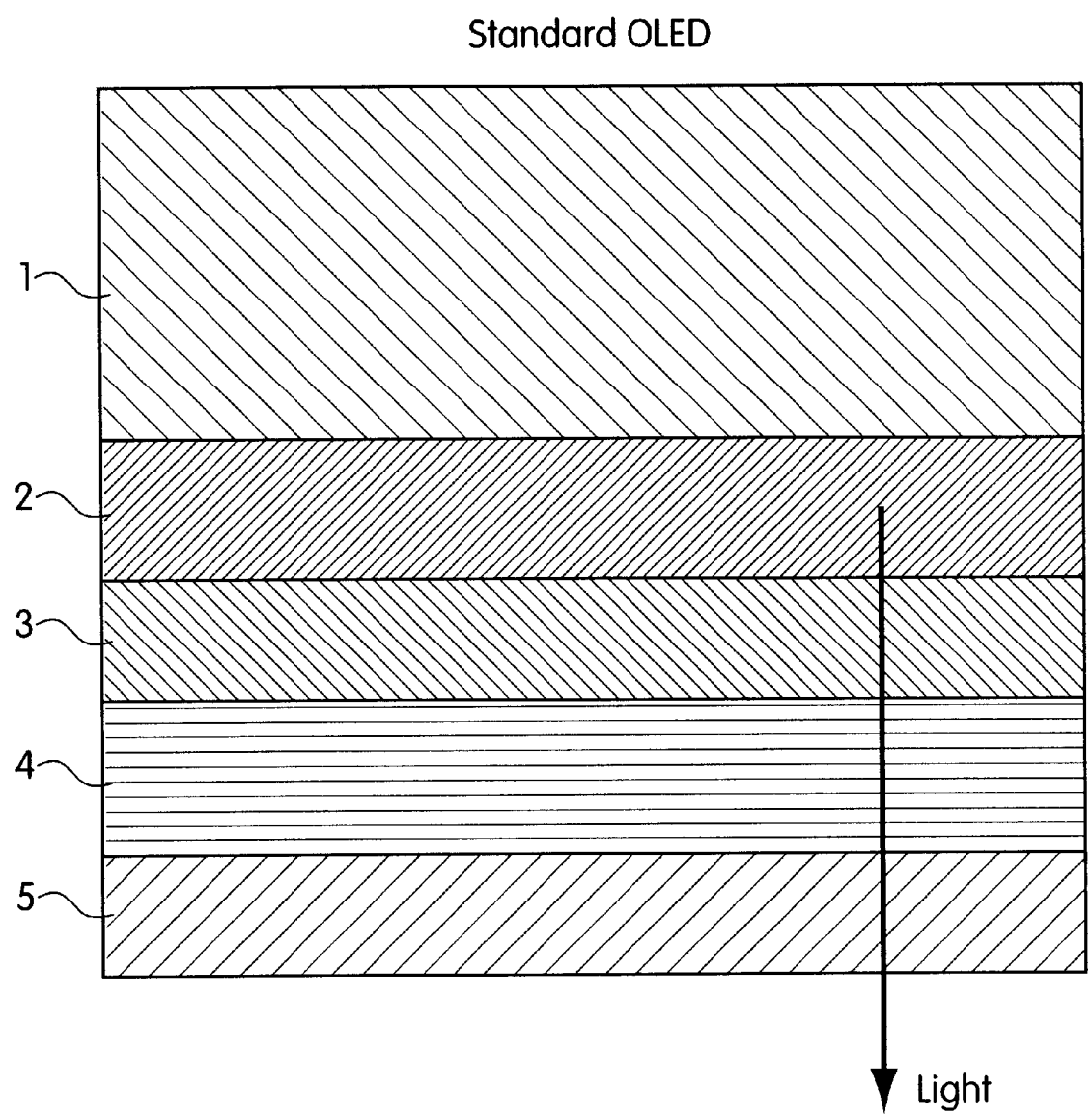
FIG. 1 shows a schematic illustration of a standard prior art OLED.

The present invention will now be described in detail for specific preferred embodiments of the invention, it being understood that these embodiments are intended only as illustrative examples and the invention is not to be limited thereto.

The present invention is directed to a novel cathodes comprised of an electrically conductive non-metallic layer which forms a low resistance electrical contact with a semiconductive organic layer. Such cathodes may be employed in a wide range of electrical devices. In particular, since the cathodes of the present invention may be fabricated from highly transparent materials, such cathodes have particular benefit for use in organic optoelectronic devices such as OLEDs, solar cells, photodetectors, lasers and phototransistors. S. R. Forrest, Chem. Rev. 97, 1793 (1997). In an optoelectronic device having at least one electron transporting layer (ETL) comprised of an electron transporting material and at least one hole transporting layer (HTL) comprised of a hole transporting material, the cathode is identified as the electrode on the ETL side of the device and the anode is identified as the electrode on the HTL side of the device. In an OLED, for example, the cathode may be referred to as the electrode that injects electrons into the ETL and the anode as the electrode that injects holes into the HTL. Injecting holes into the HTL is equivalent to extracting electrons from the HTL.

Each electrode of an OLED may typically be present as a layer that is in direct contact with the adjacent HTL or ETL, dependent on whether the electrode functions as an anode or cathode, respectively. Alternatively, it was disclosed in copending Ser. No. 08/865,491, now U.S. Pat. No. 5,998,803, that an additional organic layer may be included between the anode and the organic HTL. Such an additional layer, which was referred to as a protection layer or a hole-injection-enhancement layer, was disclosed to function as a protection layer for protecting the underlying organic layers during deposition of the electrode layer and/or as an enhancement layer for enhancing the hole-injection efficiency of the anode. For example, Ser. No. 08/865,491 (U.S. Pat. No. 5,998,803) disclosed that a protection layer, for example, of a phthalocyanine compound, such as zinc phthalocyanine (ZnPc) or copper phthalocyanine (CuPc), or PTCDA, could be deposited on top of the organic HTL so as to protect the organic layer during the subsequent sputter deposition of the ITO anode layer. Ser. No. 08/865,491 (U.S. Pat. No. 5,998,803) further disclosed that the protection layer could in some cases enhance the hole-injection efficiency of the hole-injecting anode.

Because of the combination of high electrical conductivity and low work function, which is provided by certain metals, practically useful optoelectronic devices such as OLEDs containing a cathode/organic-layer interface have until now been comprised of metallic cathode materials that inherently have a high reflectivity as well as modest absorption of optical radiation, even though the performance of such optoelectronic devices tends to be adversely affected by the high reflectivity of the metallic cathode layers. In optoelectronic devices such as OLEDs for which a high transparency is desired, semi-transparent metallic cathode layers are typically prepared using very thin metallic layers. Nevertheless, the metal's high reflectivity, which is inherently related to the high electrical conductivity of the metallic cathode materials, still causes significant losses in the overall performance of the device, for example, in producing a reduced quantum efficiency for the overall device.

One of the surprising aspects of the present invention is the fact that an electrically conductive non-metallic material has been found to be capable of forming a low-resistance electrical contact with an organic layer, wherein the electrically-conductive-non-metallic-layer/semiconductive-organic-layer interface, hereinafter "cathode/organic layer interface", is capable of efficiently injecting electrons from the non-metallic cathode layer, through the semiconductive organic layer of the cathode/organic layer interface, and then into the adjacent ETL of a practically useful organic optoelectronic device. The semiconductive organic layer of the cathode/organic layer interface is, therefore, alternatively referred to herein as the electron injecting interface layer.

For the purpose of specifying what is meant herein by a low-resistance electrical contact that may be used in a practically useful organic optoelectronic device, such a contact is one for which the voltage drop across the cathode/organic layer interface is not greater than the total voltage drop across the remainder of the device, that is, the voltage drop across the cathode/organic layer interface is less than about 50% of the total voltage drop across the overall device. Preferably, the voltage drop across the cathode/organic layer interface is less than about 30% of the total voltage drop.

The electrically conductive non-metallic layer may be selected from a wide range of non-metallic materials, wherein the term "non-metallic" is meant to embrace a wide range of materials provided that the material is free of metal in its chemically uncombined form. When a metal is present in its chemically uncombined form, either alone or in combination with one or more other metals as an alloy, the metal may alternatively be referred to as being present in its metallic form or as being a "free metal". Thus, the non-metallic cathodes of the present invention may sometimes be referred to by one or more of the inventors of the present invention as "metal-free cathodes" wherein the term "metal-free" is expressly meant to embrace a material free of metal in its chemically uncombined form. Such "non-metallic" or "metal-free" materials may also be referred to as "metal substitutes". As used herein, the term "metal substitute" refers to a material that is not a metal within the normal definition, but which has metal-like properties in appropriate contexts. Commonly used metal substitutes for electrodes would include wide band gap semiconductors, for example, transparent conducting oxides such as indium tin oxide (ITO), tin oxide (TO) and gallium indium tin oxide (GITO). In particular, ITO is a highly doped degenerate n+semiconductor with an optical band gap of approximately 3.2 eV rendering it transparent to wavelengths greater than approximately 320 nm. Another electrode material is the transparent conductive polymer polyanaline (PANI) and its chemical relatives.

It is to be understood that while the present invention relates to a non-metallic cathode material that is characterized as being free of a metal or metal alloy that is present in its metallic or chemically uncombined form, that is, free of free metal, the cathode material might include low levels of free metal in its metallic form while still falling within the scope and spirit of the present invention. Thus, while it is not presently intended or expected that the preferred cathode materials contain any free metal in metallic form, purposely adding low levels of a metal in an attempt solely to circumvent the scope of the present invention, or even to provide an as-yet-unknown benefit, would still fall fully within the scope and spirit of the present invention. The non-metallic cathode materials of the present invention may, thus, be characterized as embracing materials that are effectively free of free metal, wherein a material effectively free of free metal will correspondingly have a conductivity value which decreases as its temperature is lowered toward absolute zero. A concomitant property of non-metallic materials is that there is almost no practically detectable optical reflectivity due to the lack of partially occupied electronic conduction bands which are present in a free metal.

Another surprising aspect of the present invention is the fact that when representative embodiments of the claimed cathodes are used, for example, in an OLED, the cathode can efficiently inject electrons into the adjacent organic layer even though the non-metallic cathode material does not have the Fermi energy level that is typically provided by a low-work-function metal. Such efficient electron injection occurs in spite of the fact that a large barrier to electron injection would be expected at the cathode/organic layer interface between the electrically conductive non-metallic layer and the semiconductive organic layer. The present invention is, thus, further directed to a method for effectively reducing such barriers to electron injection.

More specifically, in the representative embodiment of the present invention as disclosed herein, the method of the present invention for producing a low-resistance electrical contact for electron flow across a cathode/organic-layer interface comprises providing a damage region at or near the surface of the semiconductive organic layer of the cathode/organic interface and, thus, between the non-metallic cathode material and the bulk of the semiconductive organic material. This damage region is prepared in such a manner that a high density of surface states or defect states for transport of electrons is produced. Though these surface states or defect states have not yet been detected directly, and may not in fact be readily observable directly, the presence of these surface states is believed to be necessary to account for the substantially reduced barrier to electron transport as evidenced indirectly by the low-resistance electrical contact across the cathode/organic layer interface.

In particular, it is believed that surface states are present at energy levels intermediate between the energy level of a conducting electron in the non-metallic cathode material and the energy level of a conducting electron in the bulk of the semiconductive organic layer of the cathode/organic interface. Furthermore, it is believed that the distribution of surface states is sufficiently dense in both energy and physical space that efficient electron transport can be effected across the cathode/organic layer interface region in spite of the large barrier to electron flow that would normally exist between a semiconductive organic material and a non-metallic material. Non-metallic cathodes having such an cathode/organic layer interface have been found, thus, to have a high efficiency, for example, for injecting electrons into the adjacent ETL of an OLED.

Furthermore, in the representative embodiment of the present invention in which ITO is used as the electrically conductive non-metallic layer and a phthalocyanine compound such as ZnPc or CuPc is used as the electron injecting interface layer, the low-resistance electrical contact is formed only when the ITO is deposited onto the organic layer and not when the organic layer is deposited onto the ITO layer. It is, thus, a further aspect of the present invention that when the preferred ITO and ZnPc or CuPc compounds are used to form the cathode/organic layer interface, the present invention is specifically directed to cathodes in which the non-metallic ITO layer is deposited onto the phthalocyanine layer using ITO deposition rates and phthalocyanine thicknesses that result in the low-resistance electrical contact. By properly controlling the ITO sputter deposition process so as to control the degree of damage caused at the surface, a cathode/organic layer interface can be produced having the desired low resistance. As described elsewhere herein, it is believed that the reduced barrier to electron transport, as evidenced by the low-resistance electrical contact, is provided by a high density of surface states at or near the surface of the organic layer. Still other methods that include the step of introducing a high density of surface states to form a cathode having a low-resistance contact between an electrically conductive non-metallic layer and a semiconductive organic layer also fall fully within the scope and spirit of the present invention.

It is believed that this feature of the present invention, that is, the ability to form a highly efficient electron-transporting cathode/organic layer interface, comparable to low-work-function metallic materials, but without the high reflectivity of metallic materials, is a uniquely advantageous combination of properties not possessed by the previously known cathode materials that were used in organic optoelectronic devices. Thus, while the present invention is described herein in terms of a specific representative embodiment thereof, it is believed that the scope and spirit of the present invention embraces any cathode comprised of an electrically conductive non-metallic layer which forms a low-resistance electrical contact with a semiconductive organic layer. Furthermore, it is believed that any method which comprises preparing surface states having a sufficiently high density to substantially reduce the barrier to electron flow between an electrically conductive non-metallic material and a semiconductive organic layer also falls fully within the scope and spirit of the present invention. A substantial reduction in the barrier to electron flow is specified herein as a reduction that results in the formation of a low-resistance electrical interface, as defined herein, between the electrically conductive non-metallic layer and the semiconductive organic layer of the cathode/organic interface. Thus, the present invention is directed to a method for fabricating a cathode comprising preparing an interface having an electrically conductive non-metallic material on one side of the interface and a semiconductive organic material on the opposite side of the interface, wherein the preparation step includes the step of forming any intermediate region between the electrically conductive non-metallic material and the semiconductive organic material such that the electrically conductive non-metallic material is capable of functioning as a cathode that forms a low-resistance electrical contact with the semiconductive organic material.

Use of electrically conductive non-metallic cathode materials that do not have the highly reflective properties inherent for metallic materials generally provides the specific benefit of being able to select highly transparent materials for use as the cathode in devices for which high optical transmission is desired, in particular, in optoelectronic devices such as OLEDs. One of the further features of the present invention is, thus, that optoelectronic devices such as OLEDs may be made using highly transparent non-metallic cathodes with electron-injection properties comparable to semi-transparent metallic cathodes. As compared with the thinnest practical semi-transparent metallic cathodes, which may typically provide a maximum transmission in the overall device of about 60–70%, devices having an optical transmission of at least about 85% may be prepared using the non-metallic cathodes of the present invention.

The electrically conductive non-metallic material that may be used to prepare the cathodes of the subject invention may be selected, for example, to be a transparent wide band gap semiconductor, for example, wide band gap semiconductor having a band gap of at least 1 eV and a transmission of at least 50% for incident and admitted radiation. Preferred wide band gap semiconductors include conductive oxides such as ITO, tin oxide, or gallium indium tin oxide (GITO).

The semiconductive organic materials that may be effectively used in combination with the ITO layer to produce the efficient electron injection preferably have the following properties:

1. A chemical and structural stability that is sufficient to permit only limited damage, as described hereinafter, due to sputtering during deposition of the ITO layer. Large planar molecules such as phthalocyanines, naphthalocyanines and perylenes are representative examples. Derivatives of these compounds with further extended conjugation (e.g., additional fused benzo-, naphtha-, anthra-, phenanthrene-, polyacene, etc., groups) may also be used. Polymeric materials may also be present under certain circumstances.

2. An electron mobility that is sufficient to permit the layer to function as an electron transporting layer; an electron transporting material having a carrier mobility with a value of at least $10^{-6}$ cm$^2$/V sec is generally believed to be sufficient for a material to function as an electron transporting layer, though substantially higher values are generally preferred; once again, large planar molecules such as the phthalocyanines and certain perylenes are representative examples.

3. The difference between the ionization potential (IP) and the HOMO/LUMO gap energy (the energy gap between the highest occupied molecular orbital and the lowest unoccupied molecular orbital), that is, the "IP-HOMO/LUMO gap energy", of the material used in the electron injecting interface layer is such that it is approximately equal to or preferably less than the IP-HOMO/LUMO gap energy of the adjacent layer into which electrons are being injected. This guideline is not intended as a constraint that is to be strictly obeyed, but is instead intended to be approximately followed. For example, small deviations from this guideline of about 0.5 eV may be tolerated for certain combinations of materials. Use of this guideline helps to prevent formation of an energy barrier to electron flow into the contacted film (e.g. Alq$_3$).

Still more specifically, the subject method may be comprised of using ITO as the electrically conductive non-metallic layer and a phthalocyanine such as CuPc or ZnPc as the electron injecting interface layer. In this case, the electrically conductive non-metallic ITO layer is sputter deposited onto an organic protection layer comprised of the electron injecting interface layer of CuPc or ZnPc. So as to control the level of damage, the ITO is sputtered onto the organic layer at relatively low initial deposition rates of about 1 to about 10 Å/minute until a thickness of about 100 Å to about 300 Å has been deposited. As described in further detail hereinafter, such an electrically-conductive-non-metallic-layer/semiconductive-organic-layer interface is capable of providing a low-resistance electrical contact for use in an OLED as well as for other types of optoelectronic devices.

The present invention is, thus, more specifically directed to a new class of highly transparent organic light emitting devices (OLEDs) employing a non-metallic cathode. OLEDs that make use of a non-metallic cathode have a very low reflectivity and a high transparency that is close to the theoretical maximum that can be achieved for a multi-layer organic structure. The low-reflectivity of such OLEDs may be particularly beneficial for use in high contrast display applications as well as for use in eliminating microcavity effects in stacked organic light emitting devices (SOLEDs). OLEDs employing these low resistance non-metallic cathodes are expected to be particularly useful in reliable high-resolution full color flat panel displays, "heads-up" displays and organic-based lasers.

Figure 2A:
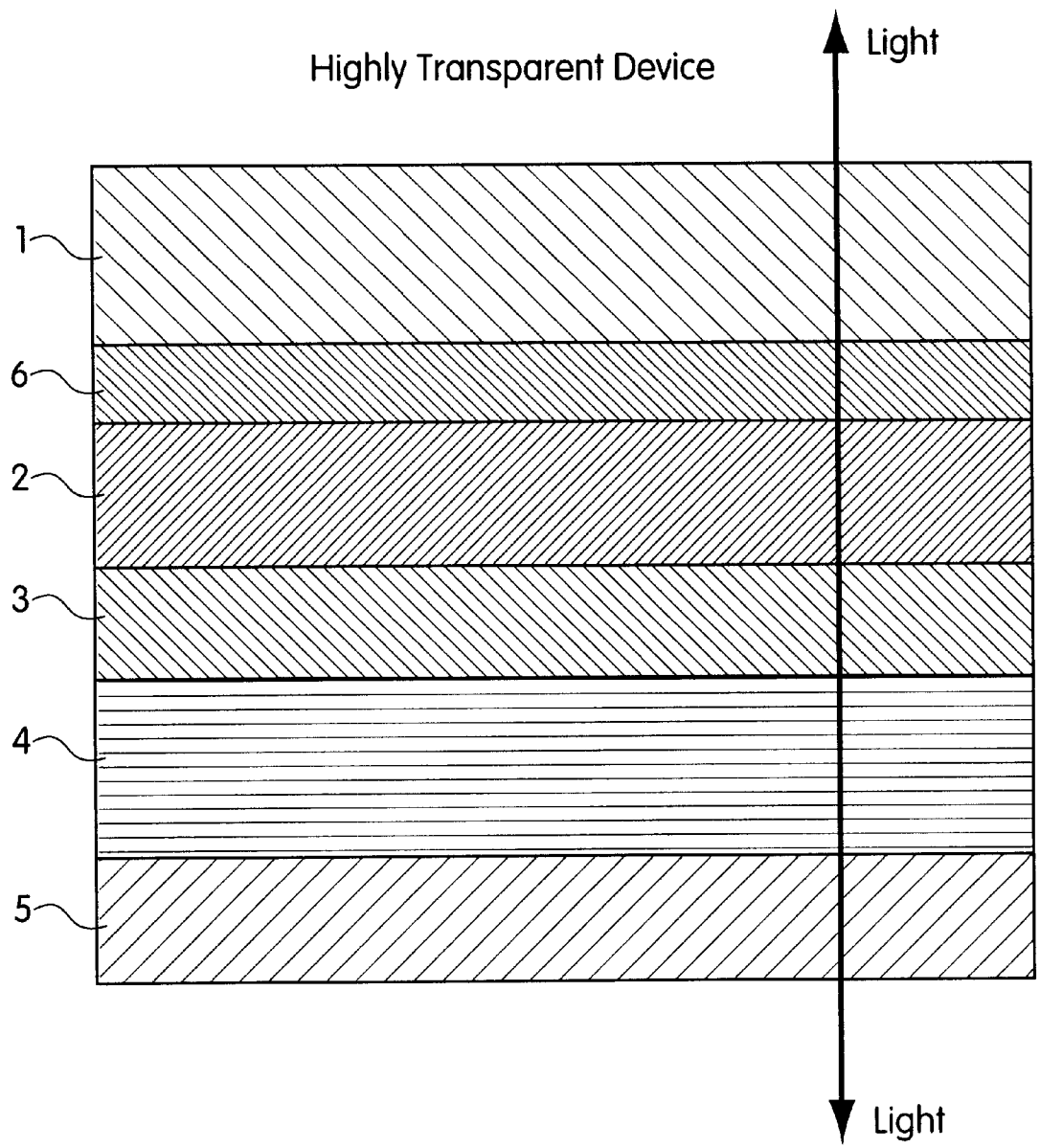
FIG. 2a shows a representative OLED of the present invention.
Figure 2B:
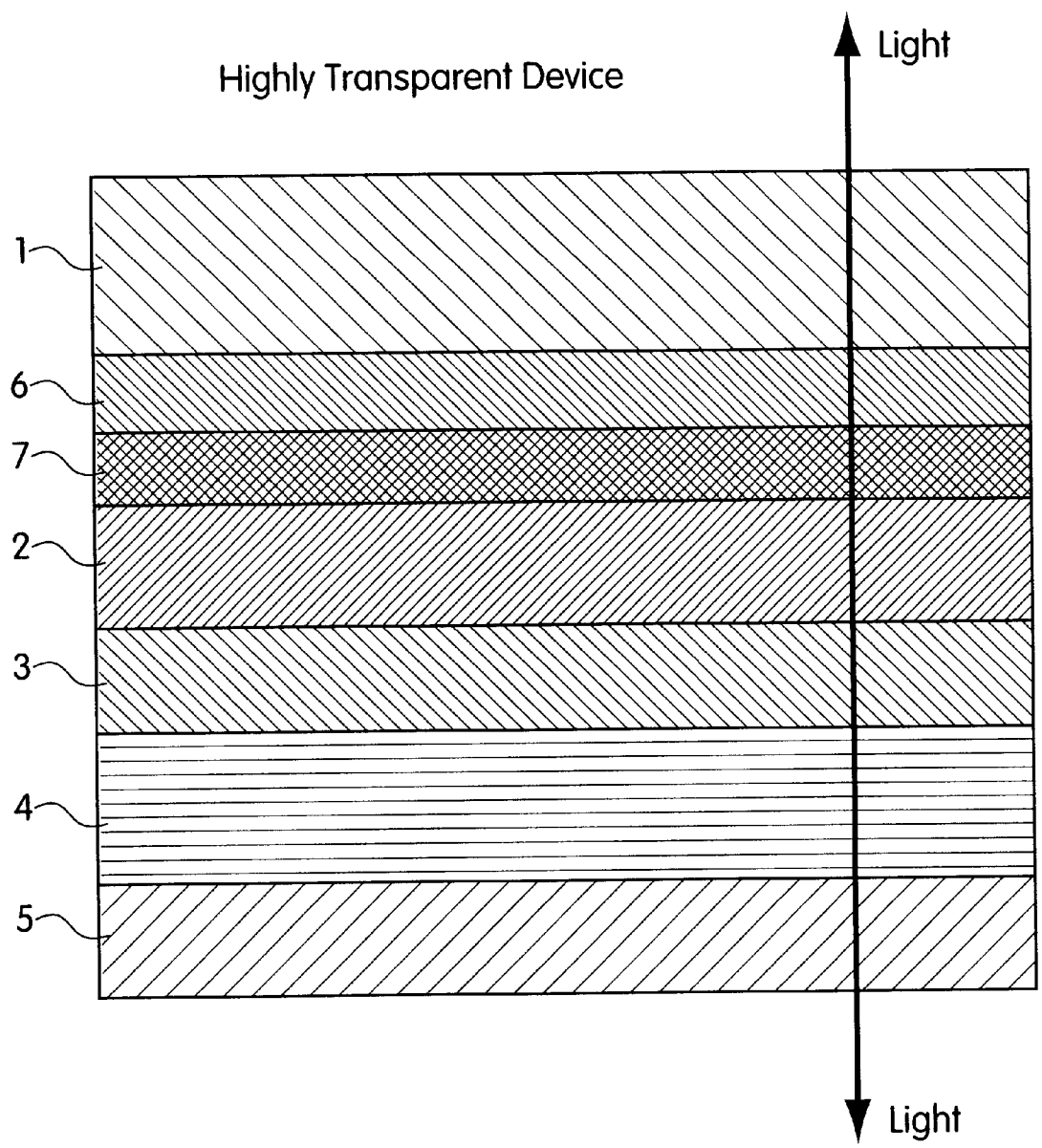
FIG. 2b shows an another representative OLED of the present invention.

As a representative embodiment of the present invention as shown in FIG. 2a, a TOLED is deposited on a glass substrate pre-coated with a film of indium tin oxide (ITO) which serves as the transparent hole injecting anode. The TOLED includes, for example, a non-metallic cathode 1, an electron injecting interface layer 6, an electron transporting layer 2, a hole transporting layer 3, an anode layer 4 and a substrate 5. After depositing a hole transporting layer and an electron transporting layer, the electron injecting interface layer is added by depositing, for example, a thin film of copper phthalocyanine (CuPc) which is then capped with a film of low-power, radio-frequency sputtered ITO. This second ITO layer functions as the cathode of this device. In addition to functioning, in some cases, as a protection layer that prevents damage to the underlying organic layers during the ITO sputtering process, the CuPc layer also functions in combination with the ITO layer as the electron injecting region for delivering electrons to the adjacent electron transporting layer. An additional intermediate electron transporting layer of 4,4'-di(N-carbazolo)diphenyl (CBP), for example, may be present between the first electron transporting layer and the CuPc layer, as shown in FIG. 2b. The intermediate electron transporting layer lies between the electron injecting interface layer that is in low-resistance electrical contact with the non-metallic cathode layer and the electron transporting layer that is in contact with the hole transporting layer. In particular, the OLED of FIG. 2b includes a non-metallic layer 1, an electron injecting interface layer 6, an intermediate electron transporting layer 7, an electron transporting layer 2, a hole transporting layer 3, an anode layer 4 and a substrate 5.

Due to the absence of a metallic cathode layer, the representative Alq$_3$-based TOLEDs disclosed herein emit nearly identical light levels in the forward and back scattered directions with a total external quantum efficiency of about 0.3%. These devices are over 80% transmissive in the visible. The reflection and absorption characteristics, current-voltage, luminance-current, and electroluminescence spectra of OLEDs prepared according to the present invention demonstrate performance characteristics that are at least comparable with and in certain respects superior to conventional TOLEDs that employ a more reflective cathode comprised of a thin film of Mg:Ag capped with ITO.

Figure 3:
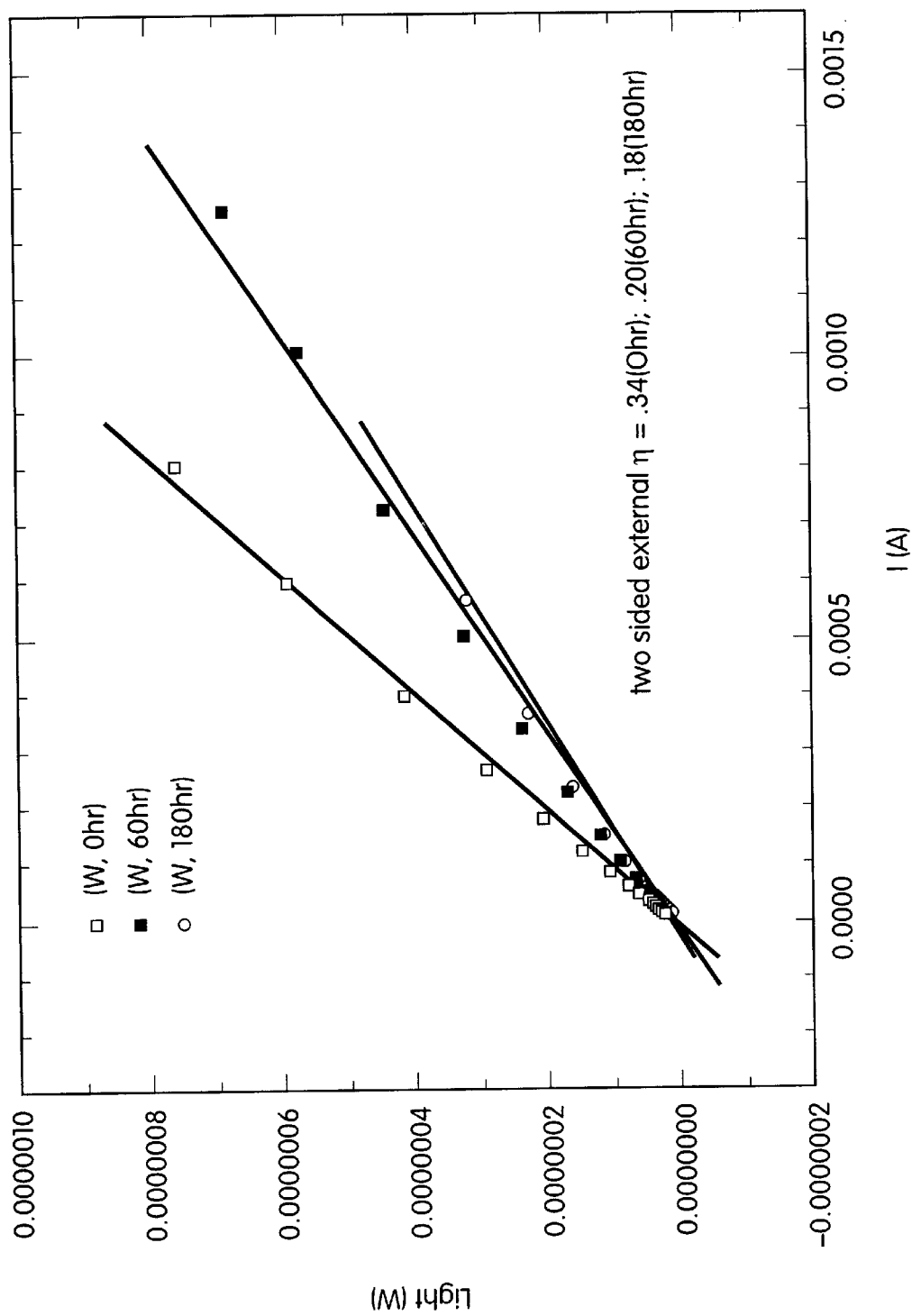
FIG. 3 shows the light output vs. current of an OLED as shown in FIG. 2a having an ITO cathode layer and a CuPc electron injecting interface layer. The lowest set of values shown in this figure was obtained at 180 hours.
Figure 4:
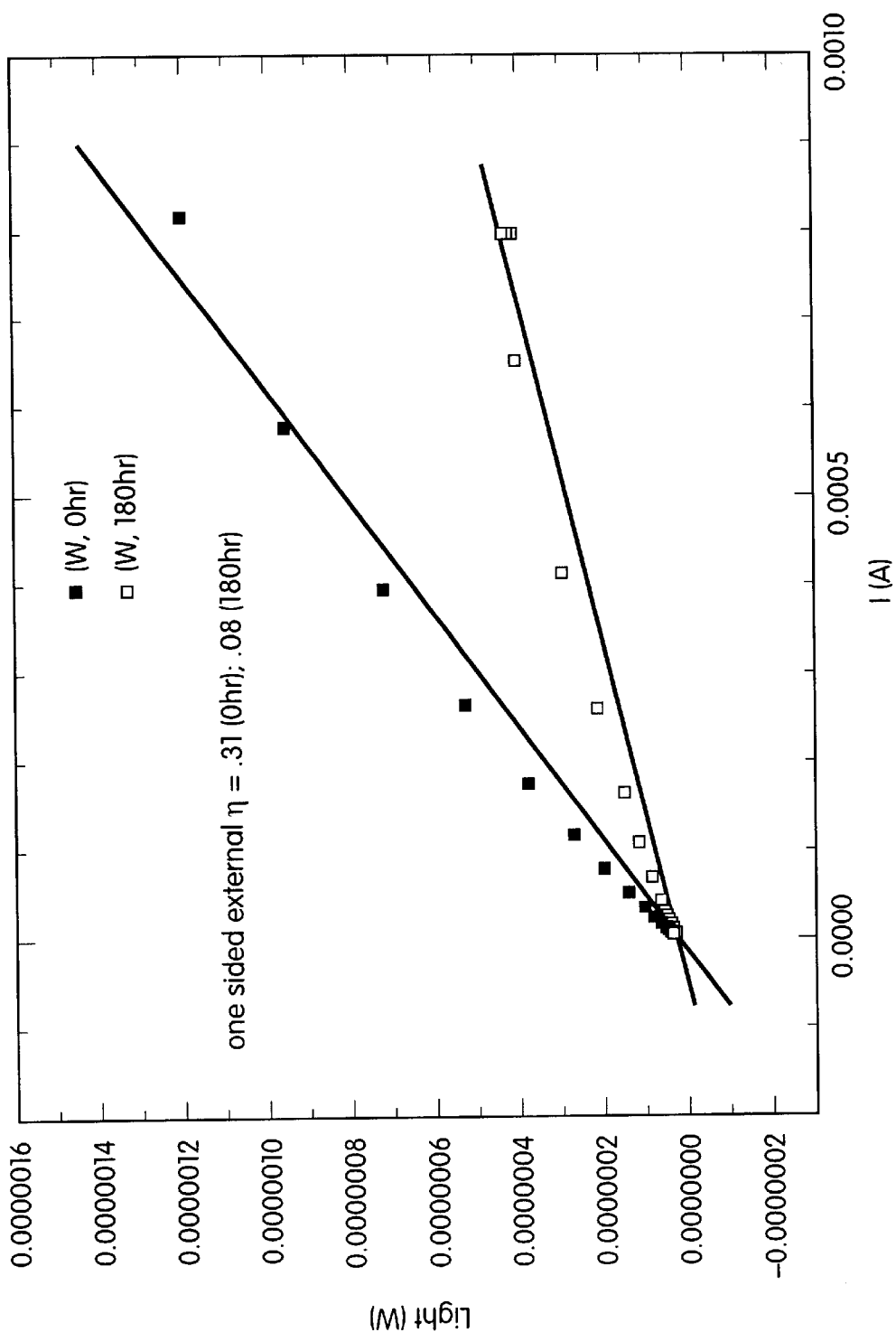
FIG. 4 shows the light output vs. current of a standard prior art TOLED device having an Mg:Ag cathode layer. The lower set of values in this figure was measured at 180 hours.
Figure 5:
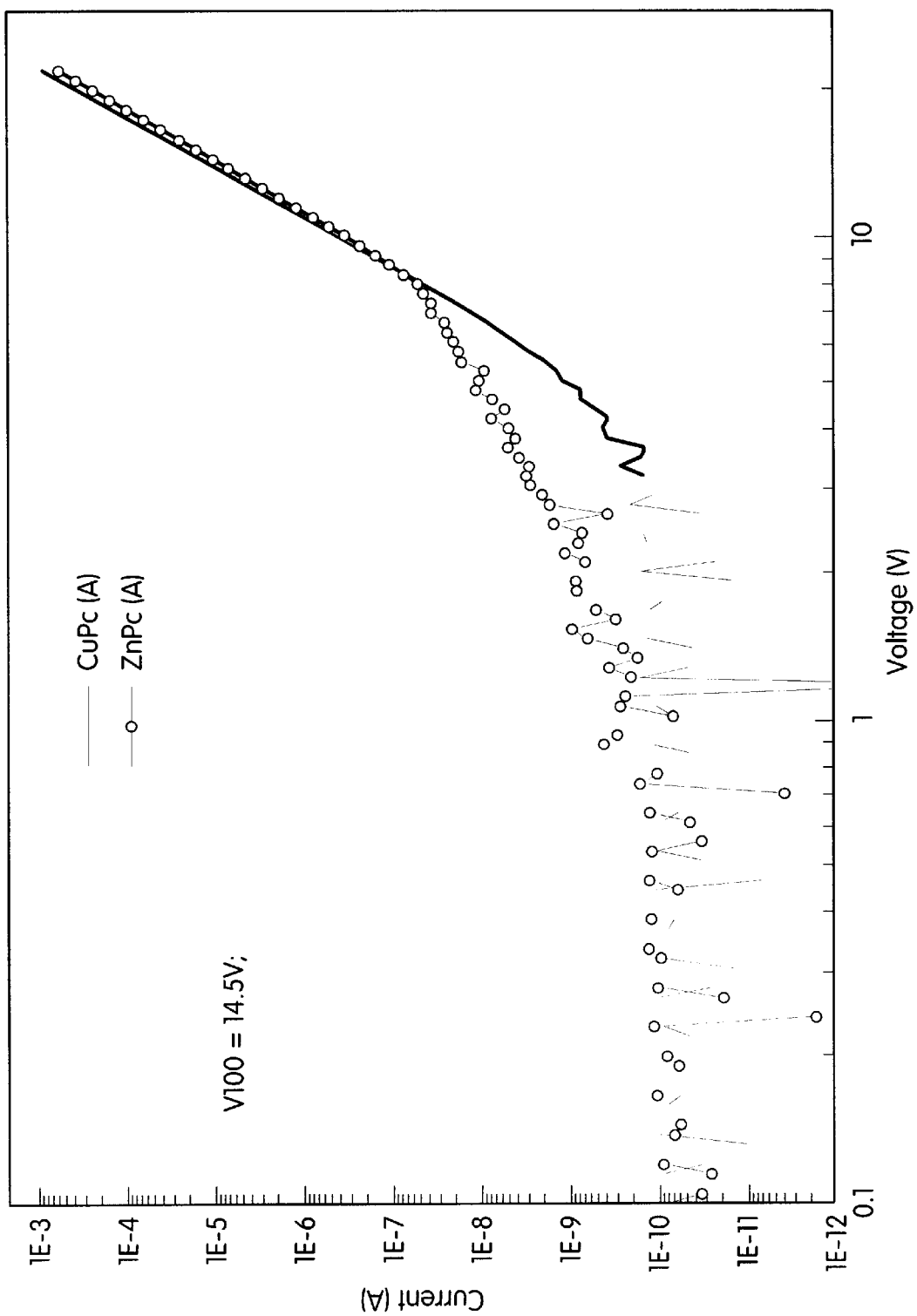
FIG. 5 shows the I–V curves for a ZnPc electron injecting interface layer and a CuPc electron injecting interface layer.
Figure 6:
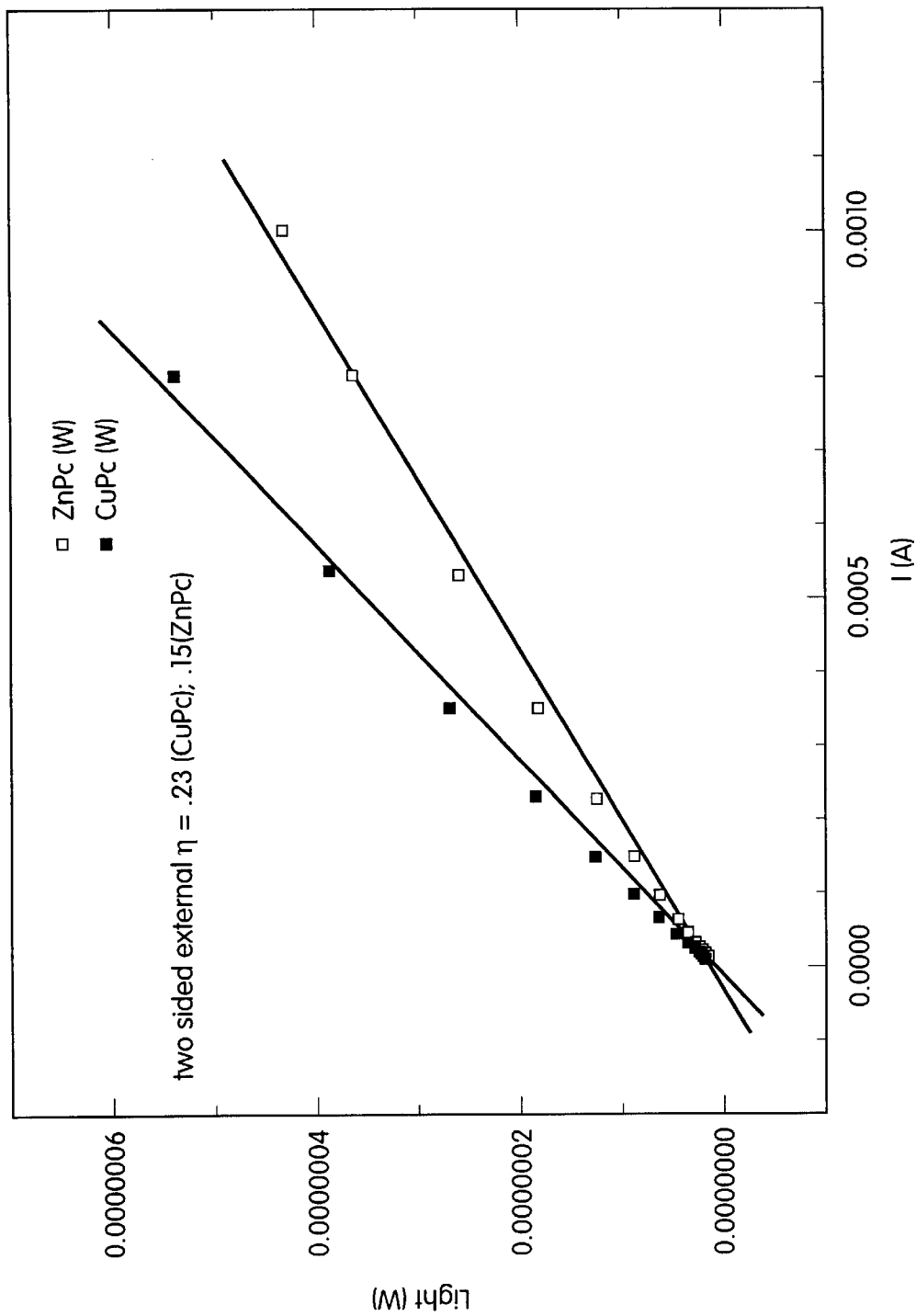
FIG. 6 shows the light output vs. current for a ZnPc electron injecting interface layer as compared with a CuPc electron injecting interface layer where the efficiency η of the CuPc device was 0.23% and the ZnPc device was 0.15%.
Figure 7:
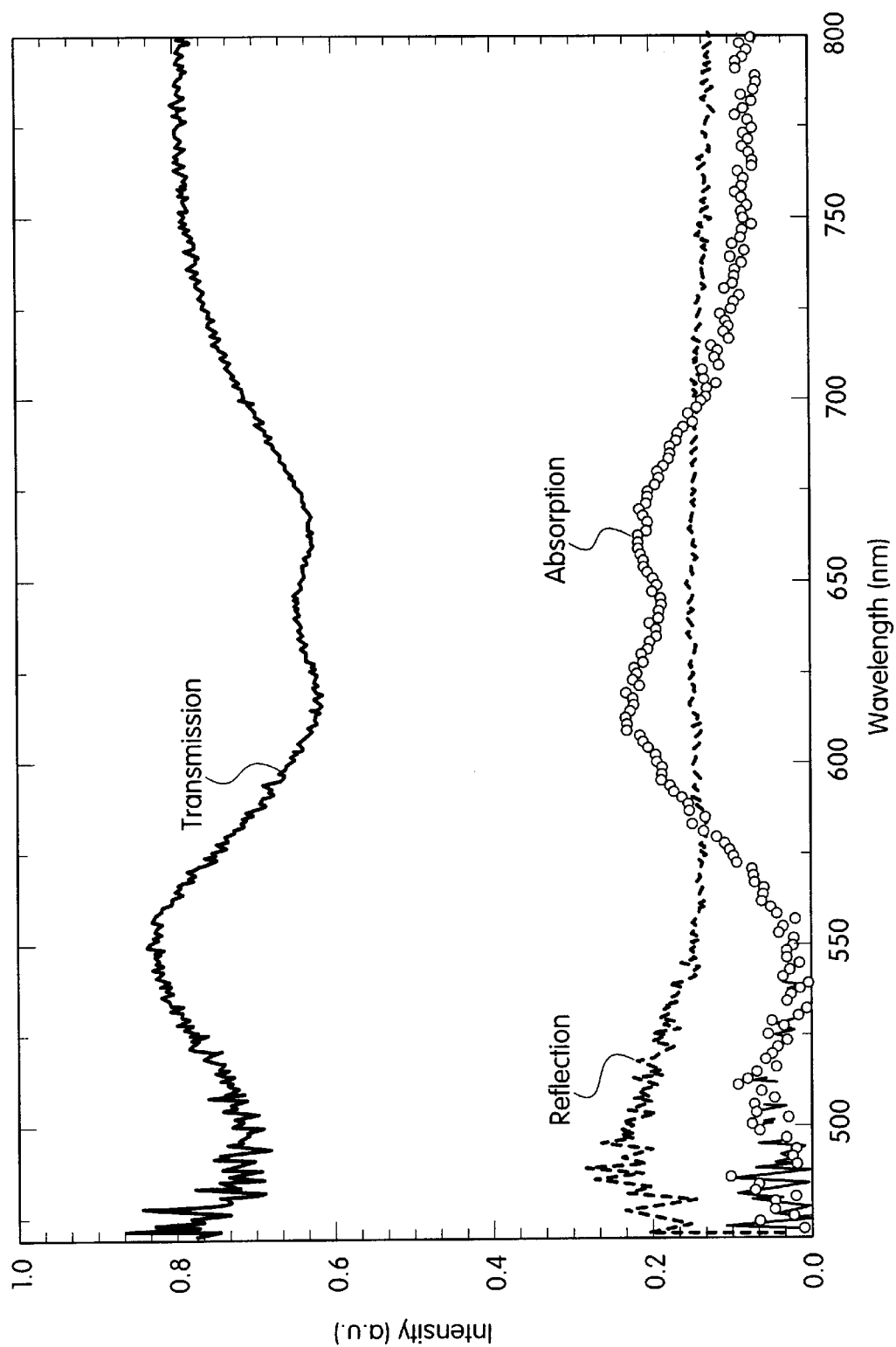
FIG. 7 shows the transmission (T), reflection (R) and absorption (A), as a function of wavelength (nm), of an OLED having an ITO cathode and CuPc electron injecting interface layer.
Figure 8:
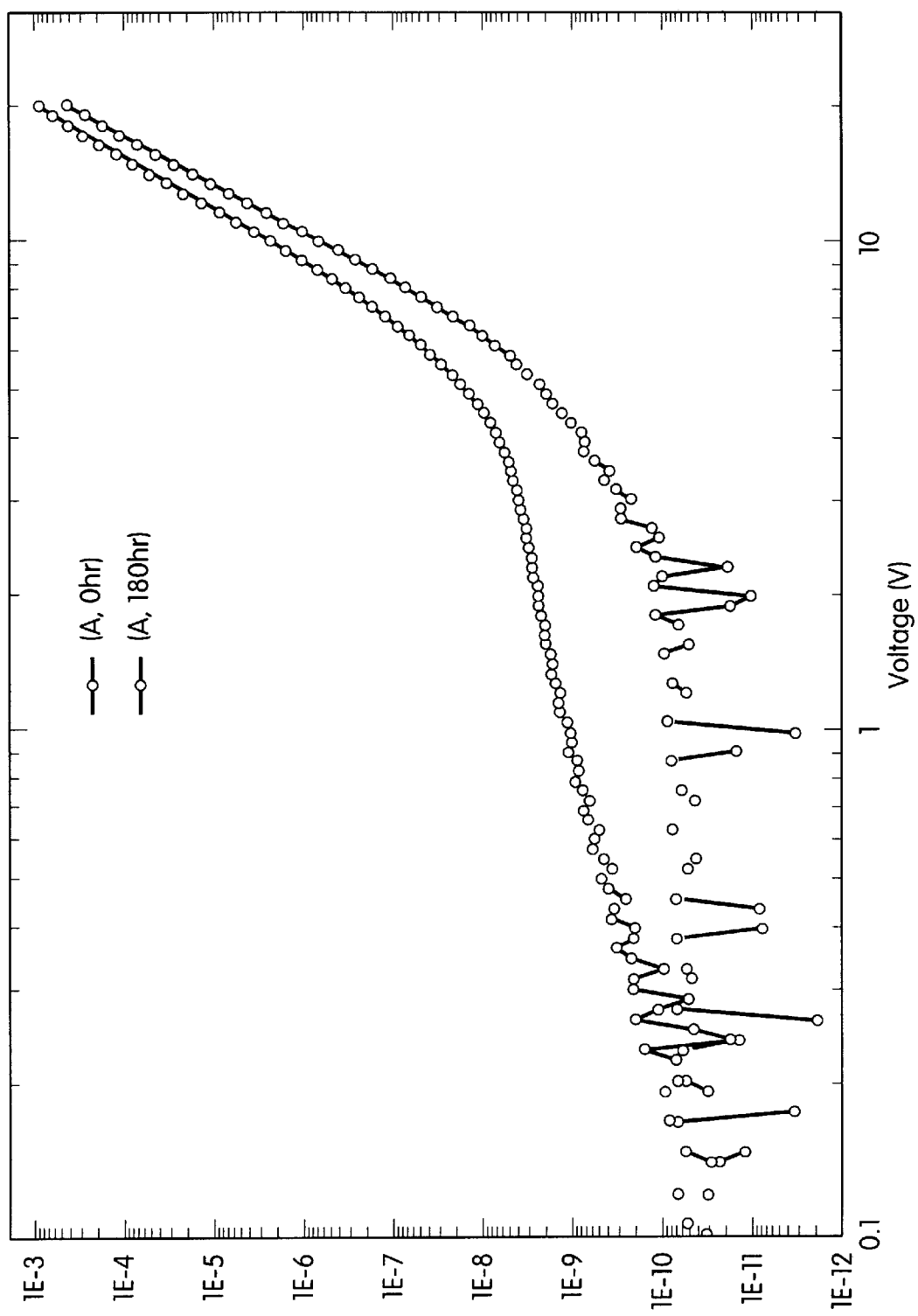
FIG. 8 shows the I–V characteristics of a standard prior art OLED having a metallic Mg:Ag cathode layer with the higher set of values at 0 hours and the lower set of values at 180 hours.
Figure 9:
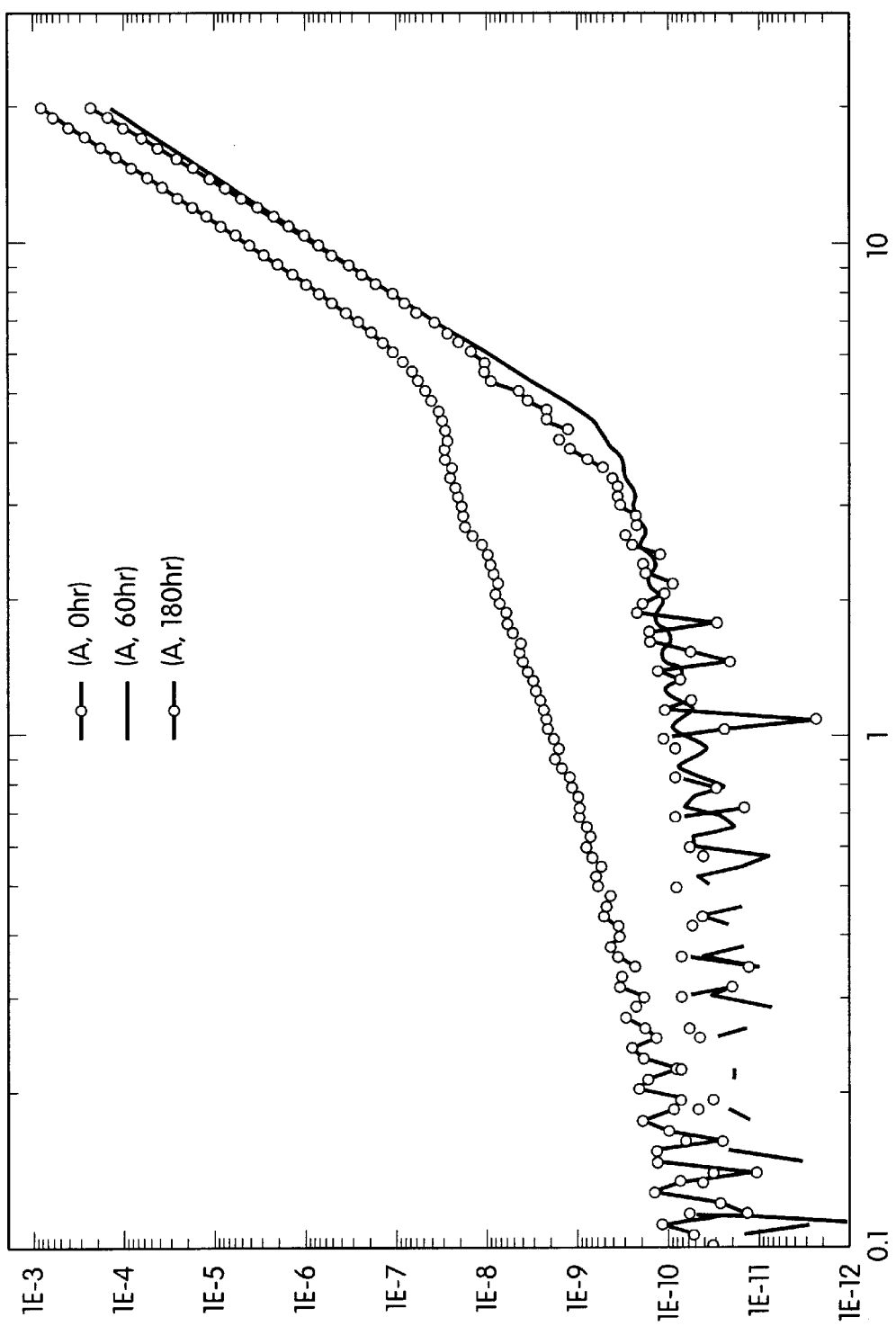
FIG. 9 shows the I–V characteristics of an OLED having an ITO cathode and a CuPc electron injecting interface layer with the higher set of values at 0 hours and the lower set of values at 60 and 180 hours.

For example, as shown by a comparison of the TOLED results shown in FIG. 3 with FIG. 4, TOLEDs according to the present invention show only about a 2-fold drop in light output at 180 hours, whereas prior art TOLEDs have about a 4-fold drop in light output over the same time interval. The results in FIG. 5 show that the phthalocyanines of both Cu (CuPc) and Zn (ZnPc) may be used as the electron injecting interface layer, though the results in FIG. 6 show that the CuPc device has a significantly higher quantum efficiency. A comparison of the results in FIG. 8 with the results in FIG. 9 shows that the stability of the I–V characteristics of OLEDs made according to the present invention is comparable to prior art devices. The results shown in FIG. 7 show that the total light transmission of an OLED made according to the present invention is near the theoretical maximum of what can be achieved for an OLED, except for that part of the spectrum which shows the Q-band absorption structure characteristic of CuPc. The reflection spectrum of this device approaches the theoretical minimum as limited by the glass/air and ITO/air interfaces. Anti-reflection layers can further reduce this reflection to a negligible value.

Figure 10:
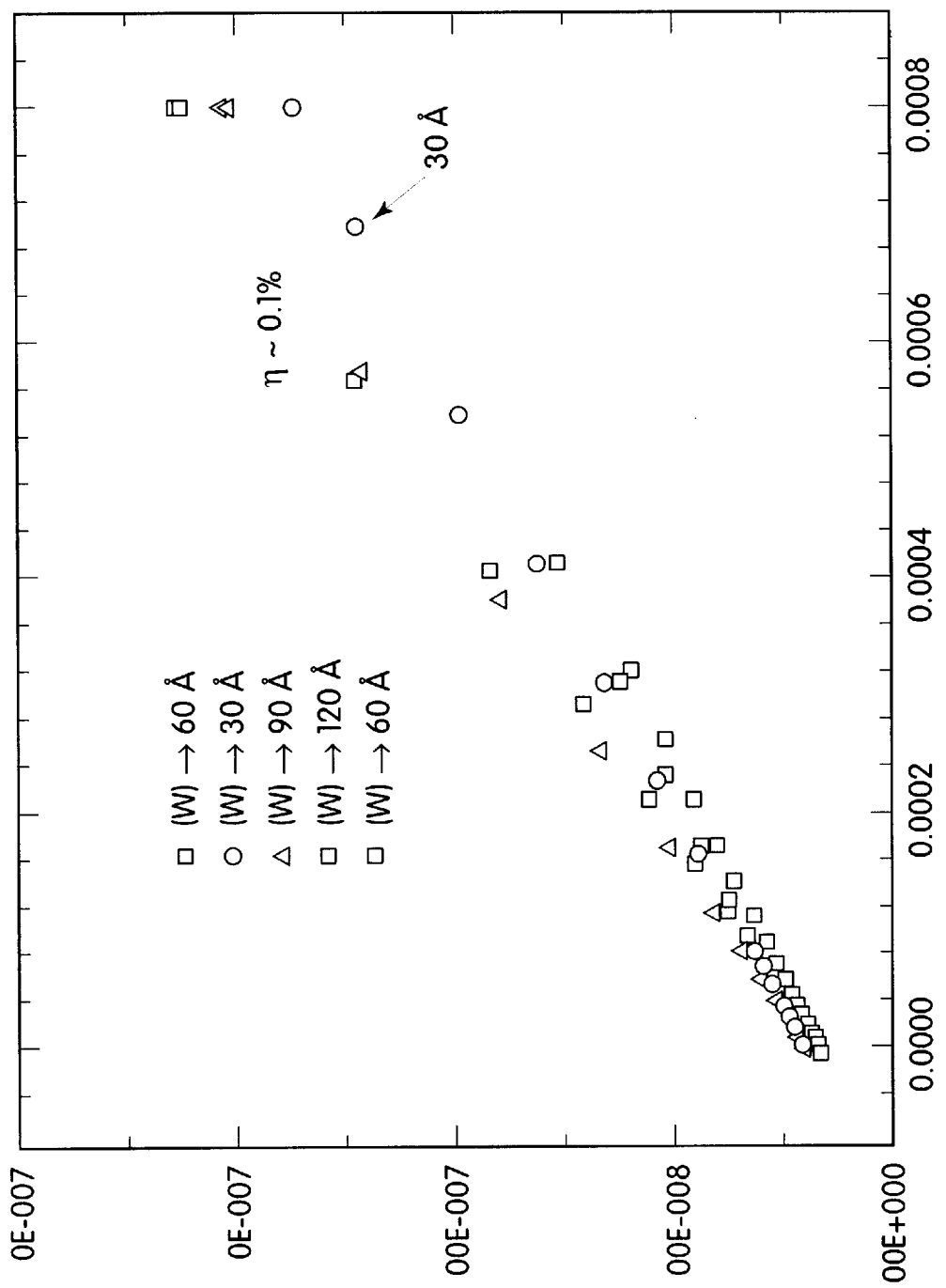
FIG. 10 shows the light output vs. current for devices having CuPc injection layer thicknesses from about 30 Å up to about 120 Å. These devices show a quantum efficiency $\eta$ of about 0.1%.
Figure 11:
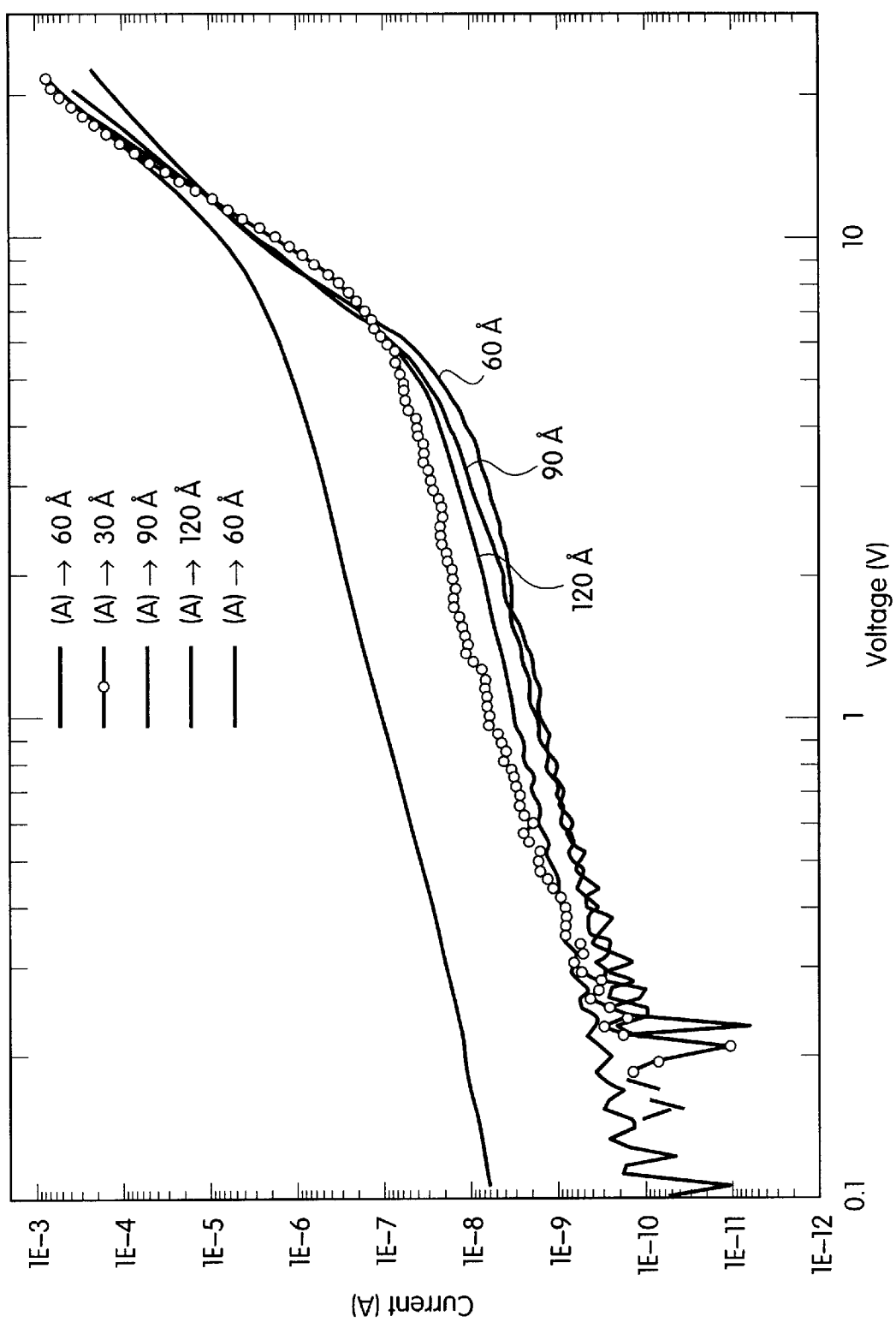
FIG. 11 shows the I–V characteristics of the devices of FIG. 10.

The electron injecting interface layer that is in contact with the ITO layer may have a thickness ranging from about 15–120 Å. For example, FIGS. 10 and 11 show that whenever CuPc is used as the electron injecting interface layer, devices having a CuPc injection layer thickness from about 30 Å to about 120 Å produced comparable performance characteristics. The devices that were prepared to collect the data shown in FIGS. 10 and 11 also included a CuPc layer with a 50 Å thickness between the ITO anode layer and the hole transporting layer. This CuPc layer, which is in contact with the ITO anode layer, functions as a hole injection enhancement layer, such as disclosed in co-pending application having Ser. No. 08/865,491, filed May 29, 1997, now U.S. Pat. No. 5,998,803.

Figure 12:
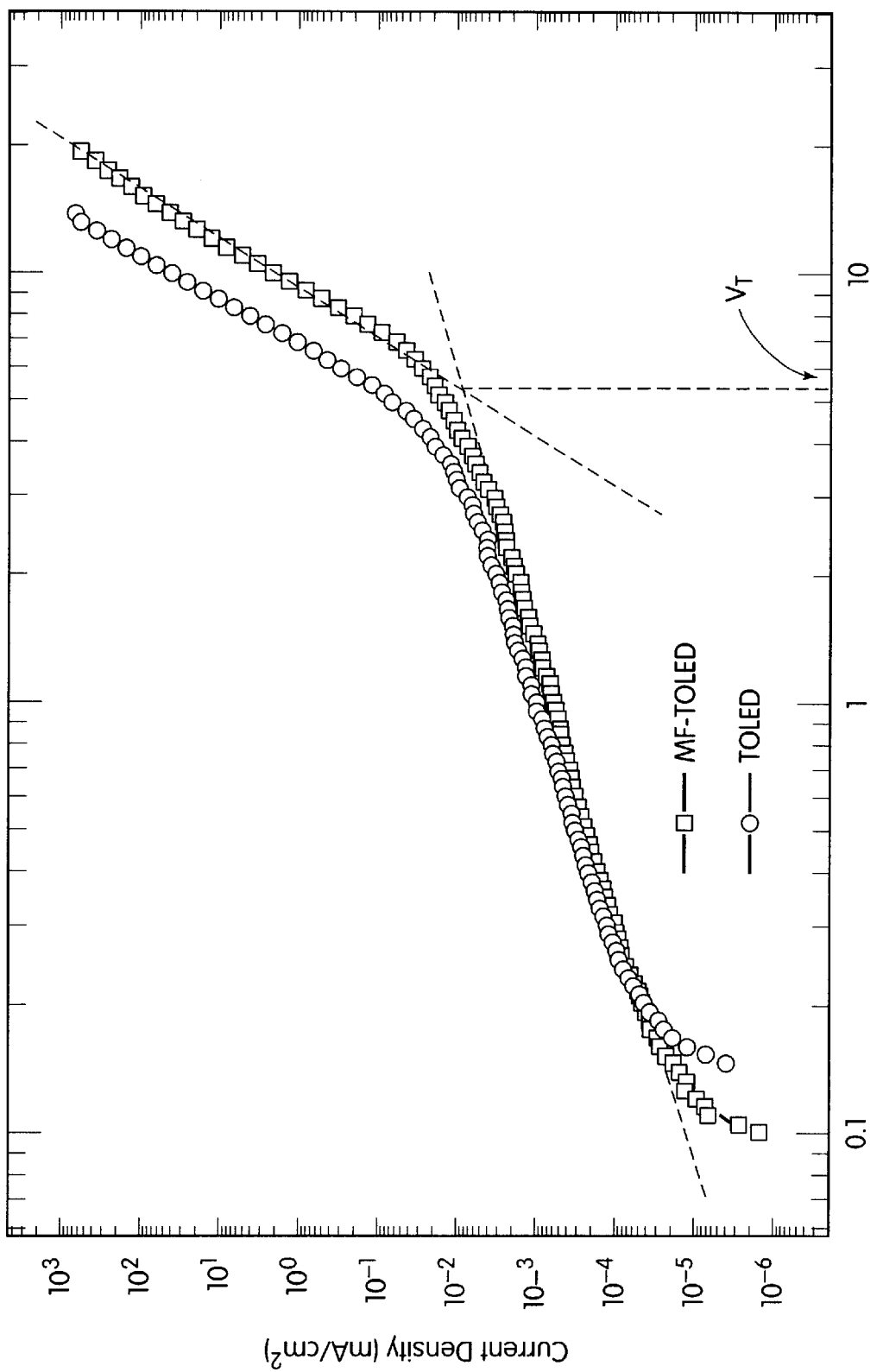
FIG. 12 shows the current-voltage characteristics of a 0.4 mm diameter non-metallic-cathode-containing TOLED ("MF-TOLED") and a reference TOLED grown in the same vacuum cycle.
Figure 13:
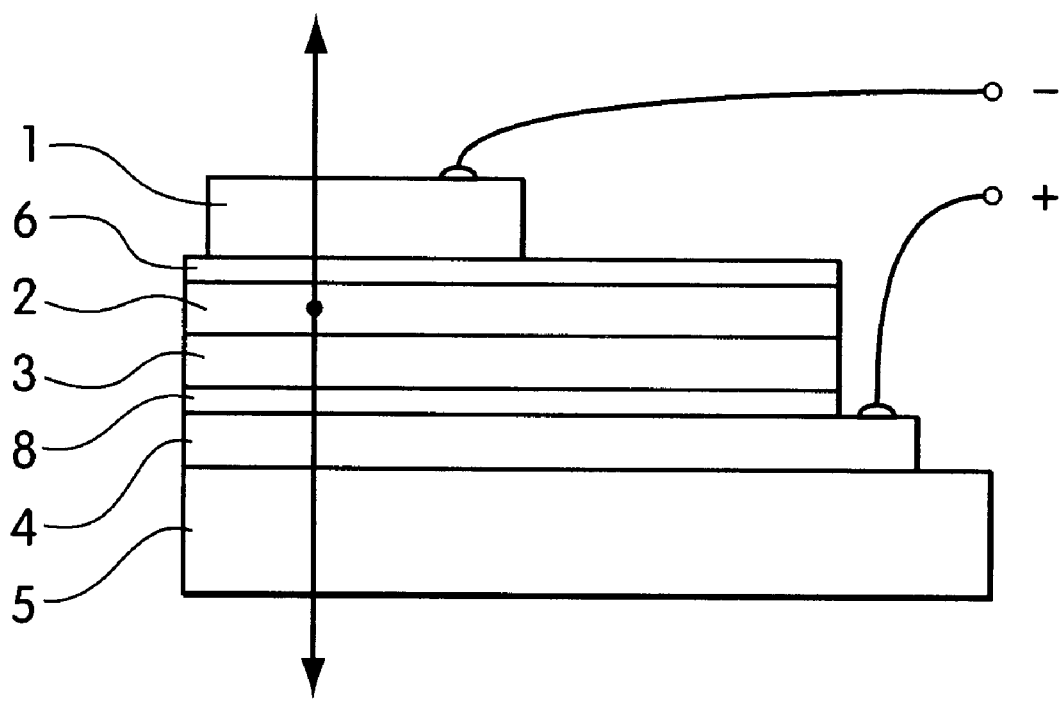
FIG. 13 shows a schematic illustration of the non-metallic-cathode-containing TOLED structure.

As further examples for representing the scope of the present invention, the current-voltage (I–V) characteristics of another typical transparent organic light emitting device having the non-metallic cathode and a conventional TOLED grown in the same run are shown in FIG. 12. The TOLED that was used to obtain the results shown in FIG. 12 is shown in FIG. 13, wherein the non-metallic cathode 1 was ITO, the electron injecting interface layer 6 was CuPc, the electron transporting layer 2 was Alq$_3$, the hole transporting layer 3 was α-NPD, the anode layer 4 was ITO and the substrate 5.

This device included an additional CuPc layer 8 between the ITO anode and HTL. Two distinct regions of operation are observed, above and below the "turn-on voltage", $V_T$. Below $V_T$, trap-free, space-charge limited transport follows I V$^{m-1}$. Above $V_T$, the current is trapped-charge-limited following I V$^{m-1}$. P. E. Burrows, S. R. Forrest, *Appl. Phys. Lett.* 64, 2285 (1994), P. E. Burrows, Z. Shen, V. Bulovic, D. M. McCarty, S. R. Forrest, J. A. Cronin, and M. E. Thompson, *J. Appl. Phys.* 79, 7991 (1996). The slightly less efficient injection properties of the ITO/CuPc as compared to those of the ITO/Mg:Ag contact are reflected in the nominal difference in $V_T$ for the TOLED (4.2 V) and non-metallic-cathode-containing TOLED (5.2 V). Similar I–V characteristics are obtained when the CuPc in the cathode is replaced with ZnPc, indicating their equivalence in forming good electron injecting contacts. However, when CuPc is replaced with PTCDA, there is a significant increase in $V_T$ to 20V.

Figure 14:
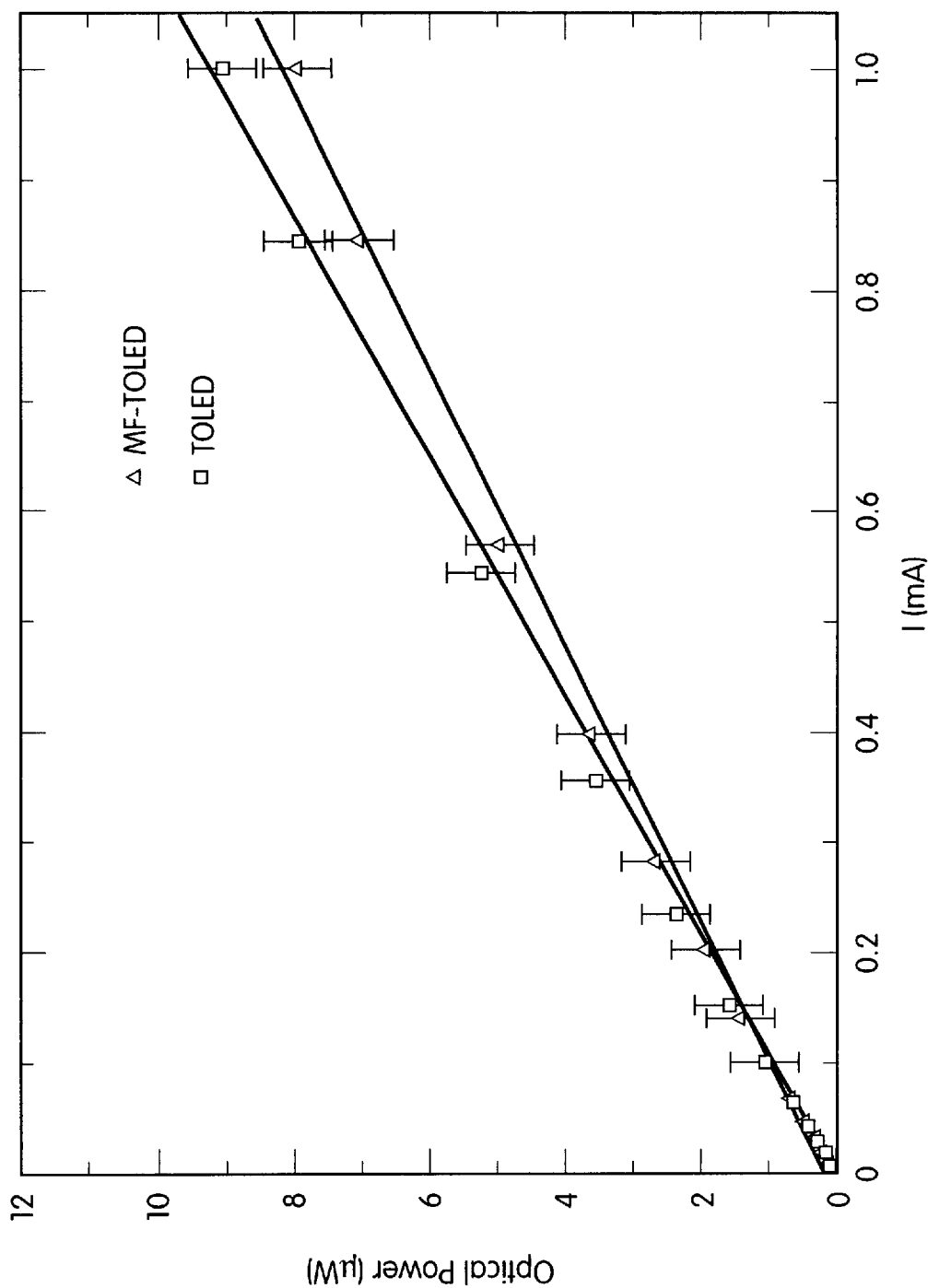
FIG. 14 shows the summed optical output power from top and bottom surfaces vs. drive current of the non-metallic-cathode-containing TOLED ("MF-TOLED") and reference TOLED in FIG. 12. The luminance at the maximum current density measured corresponds to 2000 cd/m$^2$.

The sum of the output optical power emitted from both top and bottom device surfaces as a function of the current is shown in FIG. 14 for the same devices as in FIG. 12. The total external quantum efficiencies of the devices are similar at η=(0.38±0.05) %. Their luminance at 10 mA/cm$^2$ is ~200 cd/m$^2$, increasing to 2000 cd/m$^2$ at 10 mA/cm$^2$, corresponding to the maximum drive current indicated in FIG. 14. The ratio of the power emitted from the top to that emitted from the bottom substrate surface of the non-metallic-cathode-containing TOLED is r=1.0±0.05.

Figure 15:
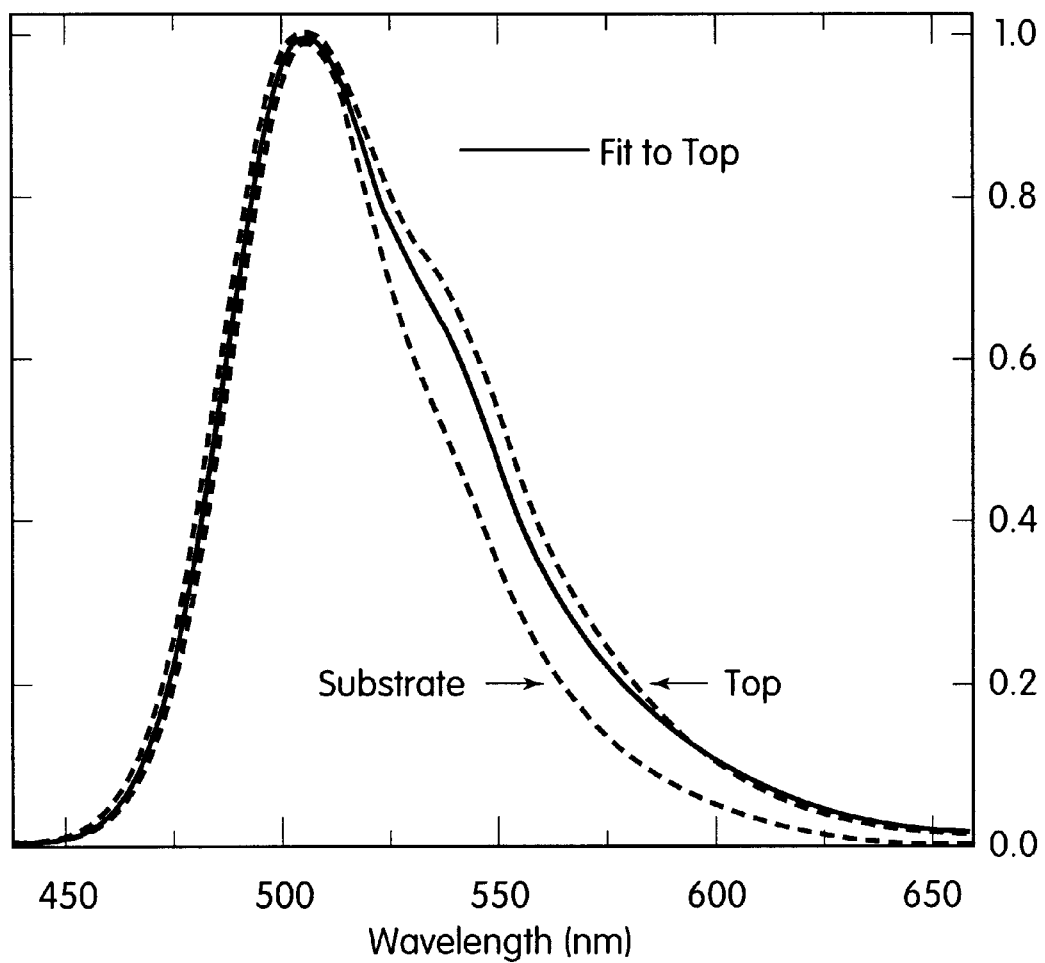
FIG. 15 shows the electroluminescence spectra from both the top and bottom device surfaces with a fit (solid line) to the top emission spectrum using the calculation method described herein.

Due to the relatively large difference between the complex index of refraction of CuPc and the other organic materials in the non-metallic-cathode-containing TOLED, there is some broadening of the output electroluminescence spectrum measured from the top, relative to the bottom device surface, as shown in FIG. 15. Using the known complex indices of refraction for each layer in the device, and assuming that the radiative, dipolar cm6 molecules are uniformly distributed in the emissive layer, r was calculated as a function of wavelength (λ). A fit to the top surface spectrum was obtained by multiplying the emission from the substrate by r(λ). The fit closely matches the normalized, measured output spectra (FIG. 14), with the remaining discrepancies between calculation and experiment due to the neglect of dispersion in the CuPc.

While the I–V characteristics of devices employing CuPc or ZnPc cathodes were similar, η of the ZnPc device was 30% lower than that of the CuPc device. In sharp contrast to the CuPc and the ZnPc cathodes, however, the devices with PTCDA in the cathode had quantum efficiencies that were only about 1% that of the CuPc devices. This indicated very poor electron injection into the ETL employing PTCDA cathodes, consistent with the I–V data.

Figure 17:
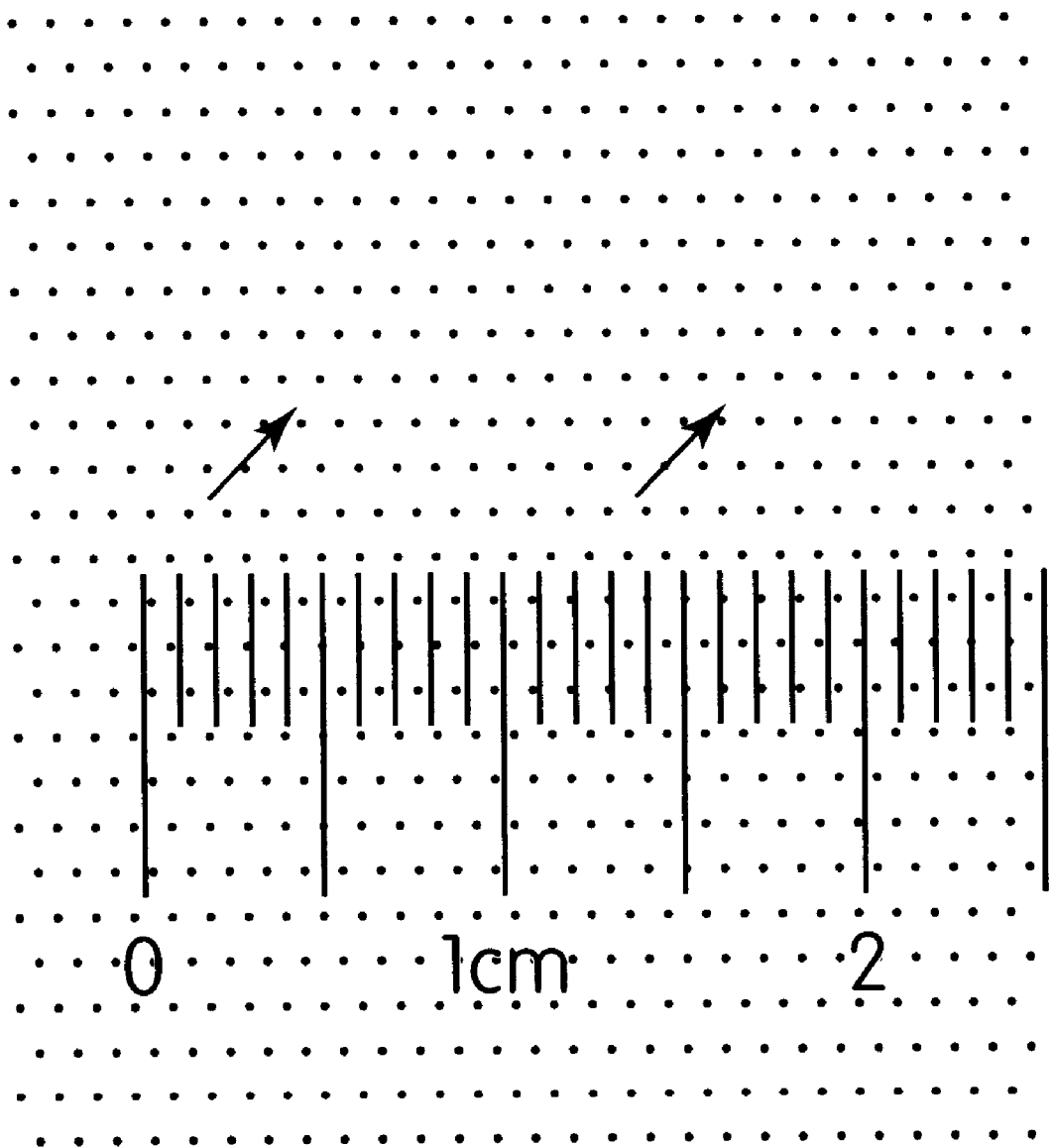
FIG. 17 shows digitally reproduced photographs that were taken of the non-metallic-cathode-containing TOLED and the conventional TOLED.

The elimination of semi-transparent metal films from the TOLED results in a significant increase in the total optical transmission. This is readily apparent from the digitally reproduced photographs that were taken of the non-metallic-cathode-containing TOLED arrays and the conventional TOLED arrays, as shown in FIG. 17. The arrays were placed on a white background having a grid of black dots for contrast. The devices were illuminated from underneath and are indicated by the arrows at about 0.2–0.4 cm for the conventional TOLED arrays and at about 1.3–1.6 cm for the non-metallic-cathode-containing TOLED arrays, respectively. The photographs in FIG. 17 show the non-metallic cathodes of the present invention are featureless due to the absence of any metal in the electrode whereas conventional TOLEDS have a faint grey appearance due to the metallic cathodes. The non-metallic-cathode-containing TOLED arrays could be detected only if the digitally Measurements of the non-antireflection-coated device optical transparency shown in FIG. 7 indicate a transmission of 0.85±0.05, which corresponds to a 35% increase over the conventional OLED. The reflection and absorption of the non-metallic-cathode-containing TOLED are also plotted in FIG. 7, where the primary source of absorption is due to the CuPc Q bands, B. H. Schechtman and W. E. Spicer, *J. of Mol. Spec.* 33, 28 (1970), which peak at λ=620 nm and 665 nm.

Without being limited to the theory of how the present invention works, it is believed that during the initial stages of ITO deposition, damage-induced states are produced in what is herein referred to as a damage layer at the cathode/organic film interface. In contrast to the prior art understanding of high efficiency electron injecting electrodes, C. W. Tang and S. A. VanSlyke, *Appl. Phys. Lett.* 51, 913 (1987), which required energy band alignment of the lowest unoccupied molecular orbital (LUMO) of the ETL with the Fermi energy of a low work function metal, it is believed herein that the damage layer is responsible for providing improved electron-injection properties for non-metallic cathodes comprised of materials that do not have the matching Fermi energy level that is typically provided by a low-work-function metal.

Figure 16:
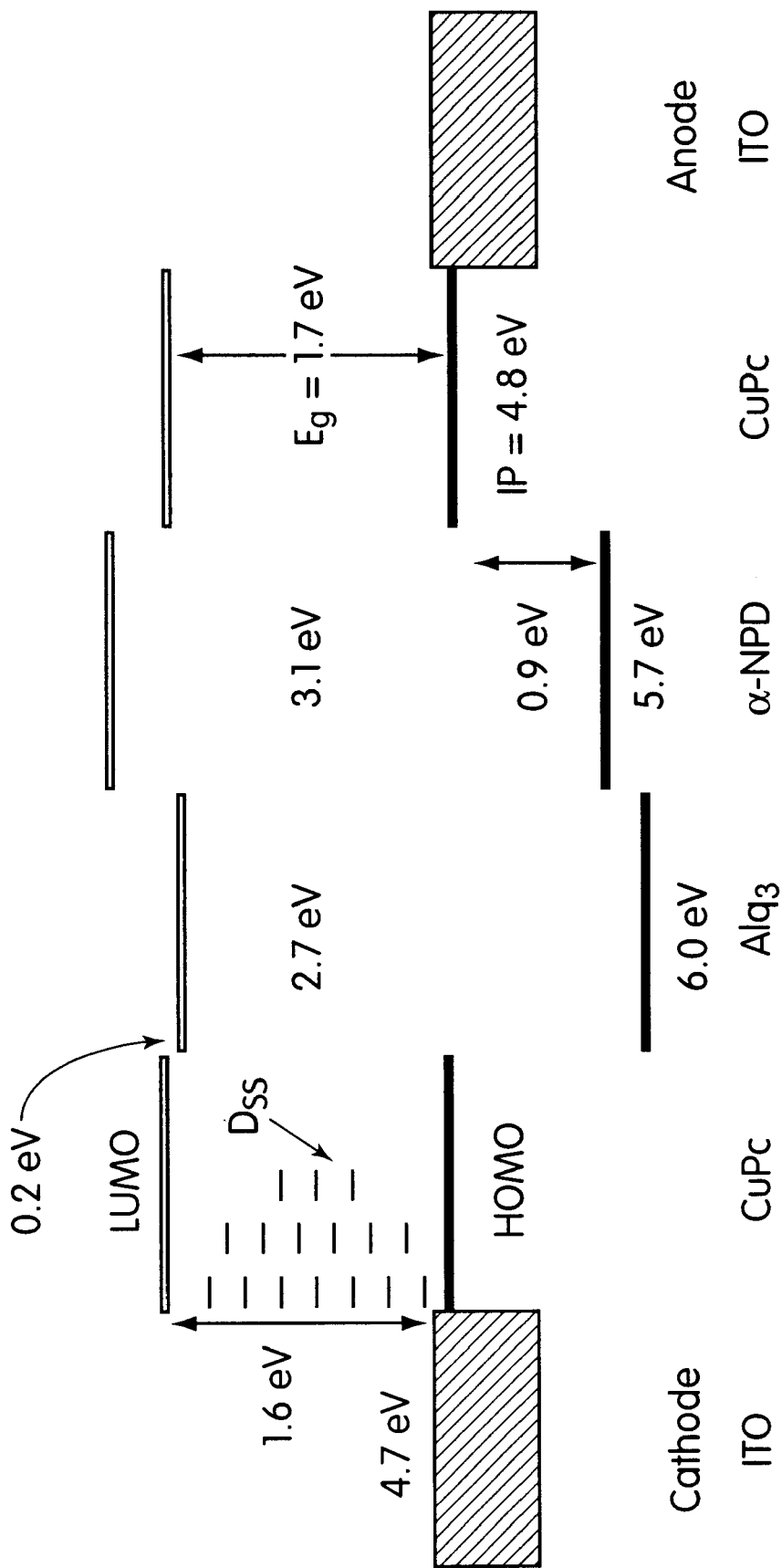
FIG. 16 shows the proposed simplified energy level diagram of a non-metallic-cathode-containing TOLED. $D_{ss}$ indicates the density of surface states.

The improved electron-injection properties of the highly transparent non-metallic cathodes may be understood in terms of the proposed energy band diagram in FIG. 16. The ionization potentials (IP), which are defined as the vacuum lever to HOMO distance, and optical energy gaps ($E_g$) are taken from A. Rajagopal, C. I. Wu, and A. Kahn, 1997 *Fall Mtg. Of Mat. Res. Soc.*, paper J1.9; and K. Seki, *Mol. Cryst. Liq. Cryst.* 171, 255 (1989). Since the ionization potential (IP) of CuPc lies between the work function of ITO and the IP of α-NPD, CuPc lowers the barrier to hole injection into the HTL. In contrast, there is a large barrier (1.6 eV) to electron injection at the ITO/CuPc interface, in spite of the fact that this electrode is disclosed herein to efficiently inject electrons whenever this electrode is prepared in accord with the present invention. This apparent contradiction is consistent with previous reports, S. R. Forrest, L. Y. Leu, F. F. So, and W. Y. Yoon, *J. Appl. Phys.* 66, 5908 (1989), of efficient hole injection using anodes consisting of PTCDA capped with ITO. In this case, hole injection is achieved although the barrier from ITO into PTCDA is 2.1 eV. Values for the ionization energies (defined as the vacuum level to HOMO distance) are from A. Rajagopal, C. I. Wu, and A. Kahn, *J. Appl. Phys.* 83, 2649 (1998) and K. Seki, *Mol. Cryst. Liq. Cryst.* 171, 255 (1989). While these authors suggest that the vacuum level may not be flat between organic heterojunctions, as shown in FIG. 4, this does not change our conclusions and hence has been omitted for simplicity.

Efficient electron injection in the presence of a large energy barrier suggests that the barrier is effectively reduced due to the electrode deposition/formation process. When the ITO is sputtered onto the CuPc surface, the Cu can form a Cu—O bond via an exothermic reaction, F. F. So and S. R. Forrest, *J. Appl. Phys.* 63, 442 (1988), thereby inducing a high density of midgap or surface states, $D_{ss}$, as shown in FIG. 16. These states, whose density decreases away from the ITO interface, provide small energy "steps" which can easily be surmounted by the injected electron. These data and the resulting model are in contrast to previous suggestions that low work function metals are required for efficient electron injection. The residual energy barrier may account, in part, for the small increase in $V_T$ for the non-metallic-cathode-containing TOLED as compared with TOLEDs not having the non-metallic cathodes of the present invention.

Evidence that such damage is effective to produce the non-metallic cathode of the present invention only when the damage is restricted to the CuPc layer was obtained by reducing the CuPc layer thickness from 60 Å to 30 Å. This reduction in thickness which resulted in a concomitant reduction in the non-metallic-cathode-containing TOLED fabrication yield from about 90% to 40%. The fabrication yield is defined as the ratio of the non-shorted, efficient devices to the total number of devices fabricated and tested. Such yields were based on test populations of 10 to 20 test devices. These results suggest that only the first few monolayers of the CuPc are damaged in low resistance cathode/organic layer interfaces, as was shown in the case of ITO/PTCDA. It is thought that when the CuPc is made too thin, the sputtered ITO can "punch through" to damage the underlying $Alq_3$. Indeed, ITO sputtered directly onto either α-NPD or $Alq_3$, wherein the ITO layer would function as an anode or a cathode, respectively, results in a yield approaching zero.

It is believed herein that the limited damage to CuPc and PTCDA may be due to the extended conjugated electron orbitals in these large planar molecules. When an energetic metal or oxygen atom is incident on one of these surface molecules during sputtering, the energy of impact is efficiently distributed over the numerous bonds in the molecular π-electron systems. In contrast, no comparably large π-electron systems exist in $Alq_3$ or α-NPD. For such molecules, the impact energy is more localized among only a few atomic sites, thereby increasing the probability for breaking a molecular bond. The planar or nearly planar stacking arrangements of crystalline molecular systems such as CuPc and PTCDA may also assist in the dissipation of energy among several neighboring molecules in the lattice.

This hypothesis, based on the role played by energetic atom-induced defects in assisting carrier injection, was tested by fabricating a transparent non-metallic-cathode-containing TOLED such as that shown in FIG. 12, except with the $Alq_3$ and α-NPD layer order reversed. For these devices having the ETL and HTL layers reversed, $V_T$ was observed to increase by a factor of two (~10V) and an external quantum efficiency η of about $10^{-3}$% was measured even though the ITO/CuPc interface is known to be excellent for injecting holes into α-NPD. The low efficiency of this device, therefore, provides clear evidence that an CuPc/ITO interface not having the damage layer is ineffective in injecting electrons into $Alq_3$. It is, therefore, concluded that the low energy deposition of CuPc on top of ITO does not generate the interfacial mid-gap states required for electron injection. Thus, since the ITO layers prepared by Karl et al and Whitlock et al were also produced by deposition of the organic layer onto the ITO layer, rather than by deposition of the ITO layer onto the organic layer so as to produce a damage layer, the ITO layers of Karl et al and Whitlock et al would be expected also not to produce the enhanced electron-injection characteristics of the present invention, whenever the electrodes of Karl et al or Whitlock et al functioned as the cathode of a solar cell.

The asymmetry in the device characteristics is also consistent with the very low current and lack of electroluminescence when the non-metallic-cathode-containing TOLED is reverse biased. In this case, the electrons are unable to traverse the 1.6 eV energy barrier from the ITO into the undamaged CuPc at the anode. Once electrons are injected into the CuPc, they are transported into the $Alq_3$ due to the lack of an energy barrier to electron transport in that direction. In contrast, a large energy barrier to electrons of 0.9 eV exists from PTCDA to $Alq_3$. This barrier, coupled with the poor electron mobility of PTCDA, results in the observed high $V_T$ and low η of $Alq_3$-based devices employing ITO cathodes in contact with PTCDA. This low efficiency does not, however, suggest that PTCDA cannot be used to make a good low resistance cathode/organic interface. In particular, these results only show that a barrier of 0.9 ev is too high between the PTCDA and the $Alq_3$. By properly matching the PTCDA with an appropriate adjacent charge-carrying layer, in accord with the guidelines provided herein for aligning the LUMO/HOMO levels, an efficient ITO/PTCDA interface may be made.

As an example of another representative OLED embodiment of the present invention, the non-metallic cathode may be used in a double heterostructure wherein a thin luminescent layer is present between the electron transporting layer and the hole transporting layer.

As another representative OLED embodiment in which an electron transporting layer is the emissive layer, the ITO layer may be in contact with the electron injecting interface layer that produces the electroluminescence and that, in addition, is in direct contact with a hole transporting layer. In this case, the IP-HOMO/LUMO gap energy of the material used in the electron injecting interface layer is such that it is approximately equal to or preferably less than the IP-HOMO/LUMO gap energy of the material in the adjacent hole transporting layer and, in addition, the ionization potential of the material in the hole transporting layer is greater than the ionization potential of the material used in the electron injecting interface layer.

As a representative embodiment of the invention in which the hole transporting layer is the emissive layer, the ITO layer may be in contact with an electron injecting interface layer that is in direct contact with a hole transporting layer that produces the electroluminescence. In this case, the IP-HOMO/LUMO gap energy of the material used in the electron injecting interface layer is also such that it is approximately equal to or preferably less than the IP-HOMO/LUMO gap energy of the material in the adjacent hole transporting layer. However, in this case, the ionization potential of the material in the hole transporting layer is less than the ionization potential of the material used in the electron injecting interface layer.

Thus, while the present invention is demonstrated for a single heterostructure in which the ITO layer is in contact with an electron injecting interface layer that is in contact with an electron transporting layer such as $Alq_3$, the present invention is directed toward any OLED comprised of a heterostructure for producing electroluminescence wherein the heterostructure includes a non-metallic cathode.

In particular, the OLEDs of the present invention are comprised of a heterostructure for producing electroluminescence which may be fabricated as a single heterostructure or as a double heterostructure. The materials, methods and apparatus for preparing the organic thin films of a single or double heterostructure are disclosed, for example, in U.S. Pat. No. 5,554,220, which is incorporated herein in its entirety by reference. As used herein, the term "heterostructure for producing electroluminescence" refers to a heterostructure that includes, for a single heterostructure, in sequence, a hole injecting anode layer, a hole transporting layer, an electron transporting layer, and a cathode layer. An additional layer or layers may be present between one or more of the sequential pairs of these layers. For example, for a double heterostructure, a separate emissive layer is included between the hole transporting layer and the electron transporting layer. This separate emissive layer may be characterized as being a "thin luminescent layer." Alternatively, or in addition, a hole injection enhancement layer may be present between the anode layer and the hole transporting layer.

The hole injecting enhancement layer may in some cases be comprised of the same material, CuPc, as is used in the electron injecting interface layer. In each case, the CuPc layer may be in direct contact with an ITO electrode, with the distinction between the two CuPc layers being that in one case the CuPc layer is in contact with an ITO layer that functions as an anode and in the other case the ITO layer functions as a cathode. In each case, the CuPc layer functions as a charge carrier and interface layer. On the one hand when in contact with the ITO anode, the CuPc layer assists in injecting and transporting holes from the anode to a hole transporting layer, and on the other hand when in contact with the ITO cathode, the CuPc layer assists in injecting and transporting electrons from the cathode to an electron transporting layer. The CuPc layer, in each case, may also function as a layer that protects any underlying organic layers, if present, from damage during the ITO deposition process. Whenever the ITO layer is present as the electrode in a SOLED structure, opposite faces of the ITO may function as an anode and cathode, respectively.

Either the anode layer or the cathode layer may be in contact with a substrate and each electrode is connected to electrical contacts which are capable of delivering a voltage across the device causing it to produce electroluminescence from either an electron transporting layer or a hole transporting layer. If the cathode layer is deposited on the substrate, the device may be referred to as having an inverted or IOLED structure. If the heterostructure for producing electroluminescence is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between adjacent electrodes of two of the OLEDs in the stack.

While the present invention is directed to OLEDs comprised of non-metallic cathode layers rather than metallic cathode layers, the OLEDs of the present invention may, under certain circumstances, be used in combination with an OLED that does contain a metallic layer, for example, as the top or bottom OLED of a SOLED. In such cases, if the cathode layer is a metal cathode layer of Mg:Ag, a metal protective layer, for example, made of a layer of Ag for protecting the Mg:Ag cathode layer from atmospheric oxidation, may also be present. The single or double heterostructures as referred to herein are intended solely as examples for showing how an OLED embodying the present invention may be fabricated without in any way intending the invention to be limited to the particular materials or sequence for making the layers shown. For example, the heterostructure typically includes a substrate which may be opaque or transparent, rigid or flexible, and/or plastic, metal or glass, in particular, a transparent polymer such as polyester, glass, sapphire or quartz, or substantially any other material that may be used as the substrate of an OLED.

Representative materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

Representative materials that are present as a glass are desirable for use in the HTL of an OLED, rather than as a crystalline or polycrystalline material, since glasses are capable of providing higher transparency as well as producing superior overall charge carrier characteristics as compared with the polycrystalline materials that are typically produced when thin films of the crystalline form of the materials are prepared. Representative materials that may be used in the hole transporting layer in a representative embodiment of the present invention include, in particular, N,N'-diphenyl-N,N'-bis(3-methylpheny)1-1'biphenyl-4,4'diamine (TPD), 4,4'-bis[N-(1-naphthyl)-N-phenyl-amino] biphenyl ($\alpha$-NPD) or 4,4'-bis[N-(2-naphthyl)-N-phenyl-amino]biphenyl ($\beta$-NPD).

Representative materials that may be used as the electron transporting layer include, in particular, tris-(8-hydroxyquinoline)-aluminum ($Alq_3$) or 4,4'-di(N-carbazolo) diphenyl (CBP).

Representative materials that may be used as the separate emissive layer, if present, include, in particular, dye-doped $Alq_3$, or substantially any other material that may be used as the separate emissive layer of an OLED.

In those cases wherein the OLEDs of the present invention are used in combination with another OLED to form a SOLED structure that contains a metallic cathode layer, the materials that may be used as the electron-injecting, metallic cathode layer may include, in particular, Mg—Ag, Li—Ag or Ca, or substantially any other material that may be used as the metallic cathode layer of an OLED.

The insulating layer, if present, may be comprised of an insulating material such as $SiO_2$, $SiN_x$ or $AlO_2$, or substantially any other material that may be used as the insulating material of an OLED, which may be deposited by a variety of processes such as plasma enhanced chemical vapor deposition (PECVD), electron beam, etc.

The OLEDs of the present invention have the advantage that they can be fabricated entirely from vacuum-deposited molecular organic materials. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as 10 $\mu$, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^{-8}$ cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the non-metallic cathode layer from about 400 Å to greater than about 1500 Å thick with about 400–1000 Å being preferred, and about 500 Å still more preferred.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED is comprised of a heterostructure for producing electroluminescence wherein the heterostructure includes a cathode comprising an electrically conductive non-metallic layer in low-resistance electrical contact with a semiconductive organic layer.

The non-metallic cathodes of the present invention may be incorporated into an optoelectronic device that is included in a vehicle, a computer, a television, a printer, a large area wall, theater or stadium screen, a billboard or a sign.

The subject invention as disclosed herein may be used in conjunction with co-pending applications: "High Reliability, High Efficiency, Integratable Organic Light Emitting Devices and Methods of Producing Same", Ser. No. 08/774,119 (filed Dec. 23, 1996), now U.S. Pat. No. 6,046,543; "Novel Materials for Multicolor LED's", Ser. No. 08/850,264 (filed May 2, 1997), now U.S. Pat. No. 6,045,930; "Electron Transporting and Light Emitting Layers Based on Organic Free Radicals", Ser. No. 08/774,120 (filed Dec. 23, 1996), now U.S. Pat. No. 5,811,833; "Multicolor Display Devices", Ser. No. 08/772,333 (filed Dec. 23, 1996), now U.S. Pat. No. 6,013,982; "Red-Emitting Organic Light Emitting Devices (LED's)", Ser. No. 08/774,087 (filed Dec. 23, 1996), now U.S. Pat. No. 6,048,630; "Driving Circuit For Stacked Organic Light Emitting Devices", Ser. No. 08/792,050 (filed Feb. 3, 1997), now U.S. Pat. No. 5,757,139; "High Efficiency Organic Light Emitting Device Structures", Ser. No. 08/772,332 (filed Dec. 23, 1996), now U.S. Pat. No. 5,834,893; "Vacuum Deposited, Non-Polymeric Flexible Organic Light Emitting Devices", Ser. No. 08/789,319 (filed Jan. 23, 1997), now U.S. Pat. No. 5,844,363; "Displays Having Mesa Pixel Configuration", Ser. No. 08/794,595 (filed Feb. 3, 1997), now U.S. Pat. No. 6,091,195; "Stacked Organic Light Emitting Devices", Ser. No. 08/792,046 (filed Feb. 3, 1997), now U.S. Pat. No. 5,917,280; "High Contrast Transparent Organic Light Emitting Device Display", Ser. No. 08/821,380 (filed Mar. 20, 1997), now U.S. Pat. No. 5,986,401; "Organic Light Emitting Devices Containing A Metal Complex of 5-Hydroxy-Quinoxaline as A Host Material", Ser. No. 08/838,099 (filed Apr. 15, 1997), now U.S. Pat. No. 5,861,219; "Light Emitting Devices Having High Brightness", Ser. No. 08/844,353 (filed Apr. 18, 1997), now U.S. Pat. No. 6,125,226; "Organic Semiconductor Laser", Ser. No. 60/046,061 (filed May 9, 1997); "Organic Semiconductor Laser", Ser. No. 08/859,468 (filed May 19, 1997), now U.S. Pat. No. 6,111,902; "Saturated Full Color Stacked Organic Light Emitting Devices", Ser. No. 08/858,994 (filed May 20, 1997), now U.S. Pat. No. 5,932,895; "An Organic Light Emitting Device Containing a Hole Injection Enhancement Layer", Ser. No. 08/865,491 (filed May 29, 1997), now U.S. Pat. No. 5,998,803; "Plasma Treatment of Conductive Layers", Ser. No. PCT/US97/10252 (filed Jun. 12, 1997); Patterning of Thin Films for the Fabrication of Organic Multi-Color Displays", Ser. No. PCT/US97/10289 (filed Jun. 12, 1997); "Double Heterostructure Infrared and Vertical Cavity Surface Emitting Organic Lasers", Ser. No. 60/053,176 (filed Jul. 18, 1997); "Oleds Containing Thermally Stable Asymmetric Charge Carrier Materials", Ser. No. 08/925,029 filed (Sep. 8, 1997), now U.S. Pat. No. 6,242,115; "Light Emitting Device with Stack of Oleds and Phosphor Downconverter", Ser. No. 08/925,403 (filed Sep. 9, 1997), now U.S. Pat. No. 5,874,803; "An Improved Method for Depositing Indium Tin Oxide Layers in Organic Light Emitting Devices", Ser. No. 08/928,800 (filed Sep. 12, 1997), now U.S. Pat. No. 5,981,306; "Azlactone-Related Dopants in the Emissive Layer of an Oled" (filed Oct. 9, 1997), Ser. No. 08/948,130, now U.S. Pat. No. 6,030,715; "A Highly Transparent Organic Light Emitting Device Employing A Non-Metallic Cathode", (filed Nov. 3, 1997), Ser. No. 60/064,005 (Provisional), "A Highly Transparent Organic Light Emitting Device Employing a Non-Metallic Cathode", (filed Nov. 5, 1997), Ser. No. 08/964,863, "Low Pressure Vapor Phase Deposition of Organic Thin Films" (filed Nov. 17, 1997), Ser. No., 08/972,156, "Method of Fabricating and Patterning Oleds", (filed Nov. 24, 1997), Ser. No. 08/977,205, now U.S. Pat. No. 6,013,538; "Method for Deposition and Patterning of Organic Thin Film", (filed Nov. 24, 1997), Ser. No. 08/976,666, now U.S. Pat. No. 5,953,587; and "Oleds Doped with Phosphorescent Compounds" (filed Dec. 1, 1997), Ser. No. 08/980,986, now U.S. Pat. No. 6,303,238; "Organic Vertical-Cavity Surface-Emitting Laser Confirmation", (filed Jan. 22, 1998), Ser. No. 09/010,594, now U.S. Pat. No. 6,160,828; "Electron Transporting and Light Emitting Layers Based on Organic Free Radicals", (filed Feb. 18, 1998), Ser. No. 09/025,660, now U.S. Pat. No. 5,922,396; and "Aluminum Complexes Bearing Both Electron Transporting, and Hole Transporting Moieties" (filed Apr. 1, 1998), Ser. No. 09/053,030; each co-pending application being incorporated herein by reference in its entirety. The subject invention may also be used in conjunction with the subject matter of each of co-pending U.S. patent application Ser. Nos. 08/354,674, 08/613,207, 08/632,322, now U.S. Pat. Nos. 5,707,745, 5,703,436, 5,757,026 (respectively), and 08/693,359 and provisional patent application Ser. Nos. 60/010,013, 60/024,001 and 60/025,501, each of which is also incorporated herein by reference in its entirety.

In addition, while the highly transparent non-metallic cathodes of the present invention are illustrated with embodiments in which the highly transparent non-metallic cathode is incorporated into an OLED, substantially any type of optoelectronic device having an anode and a cathode may include a highly transparent non-metallic cathode fabricated in accord with the present invention. In particular, the non-metallic cathodes of the present invention may be included in an OLED, a solar cell, a phototransistor, a laser or a photodetector.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

EXAMPLES OF THE INVENTION

Example 1

OLEDs were prepared using known procedures except that the OLEDs included a non-metallic ITO cathode layer rather than a metallic cathode layer. In addition, an electron injecting interface layer was present between the ITO cathode and an $Alq_3$ electron transporting layer. The ITO/Borosilicate substrates that were obtained commercially had an ITO thickness of about 1500 Å. The organic layers were thermally deposited in a standard bell-jar evaporator at pressures of $1\times10^{-6}$ torr. The alpha-NPD layer was deposited at a thickness of about 350 Å, the $Alq_3$ electron transporting layer was deposited at a thickness of about 450 Å and the copper phthalocyanine (CuPc) or zinc phthalocyanine (ZnPc) were deposited at a thickness of about 60 Å. The top ITO cathode layer was RF sputter-deposited at low powers and had a thickness of about 650 Å. OLEDs were also prepared containing a CBP layer between the CuPc layer and the $Alq_3$ layer. Such OLEDs showed performance characteristics comparable to the OLEDs in which no CBP layer was present.

The devices were characterized by measuring the current-voltage, luminance-current, electroluminescence spectra and the transmission, reflection and absorption spectra. Representative data are shown in FIGS. 3–11.

The results were compared with a standard OLED, for example, as shown in FIG. 1, which includes a metallic Mg:Ag cathode layer 1, an electron transporting layer 2, a hole transporting layer 3, an anode layer 4 and a substrate 5. The alpha-NPD hole transporting layer had a thickness of about 350 Å, the $Alq_3$ electron transporting layer had a thickness of about 450 Å and the Mg:Ag cathode layer had a thickness of about 1500 Å.

Example 2

An example of a non-metallic-cathode-containing TOLED of the present invention is shown schematically in FIG. 13. The device was grown, for example, as shown in G. Gu, V. Bulovic, P. E. Burrows, S. R. Forrest, and M. E. Thompson, *Appl. Phys. Lett.* 68, 2606 (1996), in a vacuum system with a base pressure $<10^{-7}$ Torr on a pre-cleaned glass substrate coated with ITO with a sheet resistance of $20\Omega/\square$. A 30 Å to 60 Å thick film of copper phthalocyanine (CuPc) was deposited on the ITO to improve hole injection, followed by a 350 Å to 400 Å thick film of the HTL:4,4'-bis[N-(1-napthl)-N-phenyl-amino]biphenyl($\alpha$-NPD). Next, a 400 Å to 500 Å thick film of the emissive ETL, tris-(8-hydroxyquinoline) aluminum ($Alq_3$), was grown, followed by a second 30 Å to 60 Å thick film of CuPc, S. A. Van Slyke, C. H. Chen, and C. W. Tang, *AppL. Phys. Lett.* 69, 2160 (1996). The first 200 Å of $Alq_3$ was doped to 1% (by mass) with coumarin 6 (cm6). The substrate was then transferred to the ITO sputtering chamber where 400 Å to 600 Å of ITO was radio-frequency sputtered on top of the CuPc in an Ar (200 sccm) and $O_2$(0.10 sccm) ambient at a pressure of 5 mTorr and a power of 5 W. For comparison, a conventional TOLED not having the highly transparent non-metallic cathode was fabricated along with the test device, in particular, this conventional TOLED had a similar structure with the difference that the ITO/CuPc top electrode was replaced with a 100 Å thick, semi-transparent film of Mg:Ag (30:1, mass ratio) deposited onto the $Alq_3$ surface, capped by sputtered ITO. A second series of non-metallic-cathode-containing TOLEDs was fabricated using zinc phthalocyanine (ZnPc) in place of CuPc under the top ITO layer. Finally, in a third series of devices, the electron injecting CuPc layer was replaced by a 60 Å thick layer of 3,4,9,10-perlyenetetracarboxylic dianhydride (PTCDA), which has previously been shown to be effective in protecting an underlying organic film from the damage that may otherwise be incurred during sputtering. V. Bulovic, P. Tian, P. E. Burrows, M. R. Gokhale, and S. R. Forrest, *Appl. Phys. Lett.* 70, 2954 (1997).

What is claimed is:

1. A cathode for an optoelectronic device, the cathode comprising:
    a non-metallic layer; and
    an organic layer,
        wherein the non-metallic layer is electrically conductive, and is in low-resistance electrical contact with the organic layer, and
        wherein the organic layer is semiconductive.

2. The cathode of claim 1, wherein the non-metallic layer comprises a wide band gap semiconductor having a band gap of at least 1 eV.

3. The cathode of claim 2, wherein the non-metallic layer has a transmission of at least 50% for incident and admitted radiation.

4. The cathode of claim 1, wherein the organic layer is comprised of a polyacene compound.

5. The cathode of claim 1, wherein the organic layer is comprised of a phthalocyanine compound.

6. The cathode of claim 1, wherein the organic layer is comprised of copper phthalocyanine.

7. The cathode of claim 1, wherein the organic layer is comprised of zinc phthalocyanine.

8. The cathode of claim 1, wherein the organic layer is an electron transporting material having a carrier mobility of at least $10^{-6}$ cm$^2$/V sec.

9. The cathode of claim 1, wherein the non-metallic layer comprises an oxide.

10. The cathode of claim 1, wherein the non-metallic layer comprises indium tin oxide.

11. A device for converting electrical energy into optical energy or optical energy into electrical energy comprising an optoelectronic device having a plurality of layers including a cathode layer, the cathode layer comprising:

a non-metallic layer; and an organic layer, wherein the non-metallic layer is electrically conductive, and is in low-resistance electrical contact with the organic layer, wherein the organic layer is an interface layer situated between the non-metallic layer and the next adjacent layer of the optoelectronic device, and wherein the organic layer is semiconductive.

12. The device according to claim 11 wherein the non-metallic layer is comprised of a wide band gap semiconductor having a band gap of at least 1 eV.

13. The device according to claim 12 wherein the non-metallic layer has a transmission of at least 50% for incident and admitted radiation.

14. The device according to claim 11 wherein the organic layer is comprised of a polyacene compound.

15. The device according to claim 11 wherein the organic layer is comprised of a phthalocyanine compound.

16. The device according to claim 11 wherein the organic layer is comprised of copper phthalocyanine.

17. The device according to claim 11 wherein the organic layer is comprised of zinc phthalocyanine.

18. The device of claim 11 wherein the difference between the ionization potential and the HOMO/LUMO gap energy of the semiconductive organic layer is no more than about 0.5 eV greater than the difference between the ionization potential and the HOMO/LUMO gap energy of the next adjacent layer of the optoelectronic device.

19. The device of claim 11, wherein the non-metallic layer comprises an oxide.

20. The device of claim 11, wherein the non-metallic layer comprises indium tin oxide.

21. The device of claim 11, wherein the organic layer includes a damage region at a surface of the organic layer, the damage region being in direct contact with the non-metallic layer.

22. A device for converting electrical energy into optical energy comprising an organic light emitting device having a plurality of layers including a cathode layer, the cathode layer comprising:

a non-metallic layer; and an organic layer;

wherein the non-metallic layer is electrically conductive, and wherein the non-metallic layer is in low-resistance electrical contact with the organic layer, and wherein the organic layer is an interface layer situated between the non-metallic layer and the next adjacent layer of the organic light emitting device, and wherein the organic layer is semiconductive and includes a damage region at the surface of the organic layer, the damage region being in direct contact with the non-metallic layer.

23. The device according to claim 22 wherein the non-metallic layer is comprised of a wide band gap semiconductor having a band gap of at least 1 eV.

24. The device according to claim 22 wherein the organic layer is comprised of a polyacene compound.

25. The device according to claim 22 wherein the organic layer is comprised of a phthalocyanine compound.

26. (Twice Amended) The device according to claim 22 wherein the organic layer is comprised of copper phthalocyanine.

27. The device according to claim 22 wherein the organic layer is comprised of zinc phthalocyanine.

28. A display device incorporating the device of claim 22.

29. A vehicle display panel incorporating the device of claim 22.

30. A computer display incorporating the device of claim 22.

31. A television incorporating the device of claim 22.

32. A display for a printer incorporating the device of claim 22.

33. A large display screen for displaying information to an audience incorporating the device of claim 22.

34. A billboard incorporating the device of claim 22.

35. The device of claim 22, wherein the non-metallic layer comprises an oxide.

36. The device of claim 22, wherein the non-metallic layer comprises indium tin oxide.

37. A device for converting electrical energy into coherent optical energy comprising an organic laser having a plurality of layers including a cathode layer, the cathode layer comprising:

a non-metallic layer; and an organic layer;

wherein the non-metallic layer is electrically conductive, and wherein the non-metallic layer is in low-resistance electrical contact with the organic layer, and wherein the organic layer is an interface layer situated between the non-metallic layer and the next adjacent layer of the organic laser, and wherein the organic layer is semiconductive.

38. The device according to claim 37 wherein the semiconductive organic layer is comprised of zinc phthalocyanine.

39. The device according to claim 37 wherein the organic layer is comprised of a polyacene compound.

40. The device according to claim 37 wherein the organic layer is comprised of a phthalocyanine compound.

41. The device according to claim 37 wherein the organic layer is comprised of copper phthalocyanine.

42. The device according to claim 37 wherein the organic layer is comprised of zinc phthalocyanine.

43. The device of claim 37, wherein the non-metallic layer comprises an oxide.

44. The device of claim 37, wherein the non-metallic layer comprises indium tin oxide.

45. The device of claim 37, wherein the organic layer includes a damage region at a surface of the organic layer, the damage region being in direct contact with the non-metallic layer.

46. A method of fabricating an optoelectronic device, the optoelectronic device having a plurality of layers, the method comprising the steps of:

creating an anode,
depositing the plurality of layers on the anode, whereby a heterostructure is formed for producing electroluminescence, further comprising the steps of fabricating a cathode, including:
depositing an organic layer onto the next adjacent layer of the optoelectronic device; and
depositing a non-metallic layer onto the organic layer, wherein the non-metallic layer is electrically conductive, and the step of depositing the non-metallic layer onto the organic layer forms an interface damage region between the non-metallic layer and the organic layer, whereby the interface damage region causes the non-metallic layer to be in low-resistance electrical contact with the organic layer.

47. The method according to claim 46, wherein the non-metallic layer comprises a wide band gap semiconductor having a band gap of at least 1 eV.

48. The method according to claim 47, wherein the non-metallic layer has a transmission of at least 50% for incident and admitted radiation.

49. The method according to claim 46 wherein the organic layer is comprised of a polyacene compound.

50. The method according to claim 46 wherein the organic layer is comprised of a phthalocyanine.

51. The method according to claim 46 wherein the organic layer is comprised of copper phthalocyanine.

52. The method according to claim 46 wherein the organic layer is comprised of zinc phthalocyanine.

53. The method of fabricating an optoelectronic device according to claim 46, wherein the non-metallic layer is indium tin oxide.

54. The method of fabricating an optoelectronic device of claim 53, wherein the non-metallic layer is deposited by sputtering the indium tin oxide onto the organic layer at a deposition rate between about 1 to 10 angstroms per minute until a thickness of at least about 100 angstroms has been deposited.

55. A method for fabricating a cathode comprising:
preparing a cathode comprised of an electrically conductive non-metallic layer and an organic layer, wherein the preparation process includes the step of forming an interface region between the electrically conductive non-metallic layer and the organic layer, wherein the interface region causes the electrically conductive non-metallic region to be in low-resistance electrical contact with the organic layer.

56. The method according to claim 55 wherein the electrically conductive non-metallic layer is comprised of a wide band gap semiconductor having a band gap of at least 1 eV.

57. The method according to claim 56 wherein the non-metallic layer has a transmission of at least 50% for incident and admitted radiation.

58. The method for fabricating a cathode according to claim 55 wherein the organic layer is comprised of a polyacene compound.

59. The method for fabricating a cathode according to claim 55 wherein the semiconductive organic layer is comprised of a phthalocyanine compound.

60. The method for fabricating a cathode according to claim 55 wherein the organic layer is comprised of copper phthalocyanine.

61. The method for fabricating a cathode according to claim 55 wherein the organic layer is comprised of zinc phthalocyanine.

62. A cathode for an optoelectronic device, the optoelectronic device having a plurality of layers, the cathode comprising:
a non-metallic layer, wherein the non-metallic layer is electrically conductive;
a semiconductive organic layer; and
an interface damage region;
wherein the interface damage region joins the non-metallic layer to the semiconductive organic layer, the interface damage region reduces the barrier to electron transport between the non-metallic layer and the semiconductive organic layer, and the semiconductive organic layer is an interface layer between the non-metallic layer and the next adjacent layer of the optoelectronic device.

63. The cathode according to claim 62 wherein the non-metallic layer is comprised of a wide band gap semiconductor having a band gap of at least 1 eV.

64. The cathode according to claim 63 wherein the non-metallic layer has a transmission of at least 50% for incident and admitted radiation.

65. The cathode according to claim 62 wherein the semiconductive organic layer is comprised of a polyacene compound.

66. The cathode according to claim 62 wherein the semiconductive organic layer is comprised of a phthalocyanine.

67. The cathode according to claim 62 wherein the semiconductive organic layer is comprised of copper phthalocyanine.

68. The cathode according to claim 62 wherein the semiconductive organic layer is comprised of zinc phthalocyanine.

69. An organic light emitting device having a plurality of layers, the plurality of layers comprising a heterostructure for producing electroluminescence, wherein the heterostructure incorporates at least one emissive layer and a transparent cathode layer, the transparent cathode layer comprising:
a non-metallic layer; and
an organic layer;
wherein the cathode layer has at least a 50% transmission of incident and admitted radiation,
wherein the non-metallic layer is electrically conductive,
wherein the organic layer is an interface layer situated between the non-metallic layer and the at least one emissive layer of the organic light emitting device,
wherein a low-resistance electrical interface is present between the electrically conductive non-metallic layer and the organic layer, and the organic layer acts to aid the injection of electrons into the at least one emissive layer of the heterostructure.

70. An organic laser including the light emitting device of claim 69.

* * * * *